United States Patent
Clem et al.

(10) Patent No.: US 9,681,884 B2
(45) Date of Patent: Jun. 20, 2017

(54) SURGICAL INSTRUMENT WITH STRESS SENSOR

(75) Inventors: William E. Clem, Bozeman, MT (US); William D. Dannaher, Suzhou (CN); Daniel W. Price, Loveland, OH (US); Cory G. Kimball, Cincinnati, OH (US); Foster B. Stulen, Mason, OH (US); Eitan T. Wiener, Cincinnati, OH (US); John B. Schulte, West Chester, OH (US); Danius P. Silkaitus, Seattle, WA (US); Stephen J. Balek, Springboro, OH (US); Michael R. Lamping, Cincinnati, OH (US); Jacqueline C. Aronhalt, Loveland, OH (US)

(73) Assignee: Ethicon Endo-Surgery, LLC, Guaynabo, PR (US)

( * ) Notice: Subject to any disclaimer, the term of this patent is extended or adjusted under 35 U.S.C. 154(b) by 1178 days.

(21) Appl. No.: 13/484,563

(22) Filed: May 31, 2012

(65) Prior Publication Data

US 2013/0324991 A1  Dec. 5, 2013

(51) Int. Cl.
*A61B 17/32* (2006.01)
*A61B 18/14* (2006.01)
(Continued)

(52) U.S. Cl.
CPC .. *A61B 17/320068* (2013.01); *A61B 18/1402* (2013.01); *A61B 2017/00473* (2013.01);
(Continued)

(58) Field of Classification Search
CPC ........ A61B 17/320068; A61B 18/1402; A61B 2017/00473; A61B 2019/464
See application file for complete search history.

(56) References Cited

U.S. PATENT DOCUMENTS 5,951,581 A * 9/1999 Saadat ............ A61B 17/32002
604/22
5,980,510 A 11/1999 Tsonton et al.
(Continued)

FOREIGN PATENT DOCUMENTS

| EP | 2062544 | 5/2009 |
| JP | 2001 153662 | 6/2001 |
| WO | WO 97/24073 | 7/1997 |

OTHER PUBLICATIONS

International Search Report dated Nov. 21, 2013 for Application No. PCT/US2013/042668.
(Continued)

*Primary Examiner* — Amanda Patton
(74) *Attorney, Agent, or Firm* — Frost Brown Todd LLC

(57) ABSTRACT

An apparatus includes an end effector, an energy component, a control module, and a directional force sensor assembly associated with the energy component and control module. The directional force assembly can include a piezoelectric disc, a piezoresistive element, an accelerometer, and/or a Hall Effect sensor. The end effector of the apparatus can include ultrasonic blade, an RF electrode, or a staple driving assembly. In some versions, the energy component includes an ultrasonic transducer. The control module may be configured to operate the energy component at a first energy setting in response to a first detected force and at a second energy setting in response to a second detected force. The apparatus may also include an activation feature to be operated by a user. In some versions the piezoelectric disc may include a plurality of segments and may be configured to induce movement in at least part of the energy component.

21 Claims, 22 Drawing Sheets

(51) Int. Cl.
  *A61B 17/00*  (2006.01)
  *A61B 18/00*  (2006.01)
  *A61B 90/00*  (2016.01)

(52) U.S. Cl.
  CPC .............. *A61B 2018/00702* (2013.01); *A61B 2018/00708* (2013.01); *A61B 2018/00988* (2013.01); *A61B 2090/064* (2016.02)

(56) References Cited

U.S. PATENT DOCUMENTS

| | | | |
|---|---|---|---|
| 6,500,176 B1* | 12/2002 | Truckai | A61B 18/1445 606/205 |
| 6,585,668 B2 | 7/2003 | Nissim | |
| 6,783,524 B2 | 8/2004 | Anderson et al. | |
| 7,416,101 B2 | 8/2008 | Shelton, IV et al. | |
| 7,473,251 B2 | 1/2009 | Knowlton et al. | |
| 7,738,971 B2 | 6/2010 | Swayze et al. | |
| 7,955,327 B2* | 6/2011 | Sartor | A61B 18/1402 606/34 |
| 8,016,824 B2* | 9/2011 | Buchman, II | A61B 18/1402 606/38 |
| 2005/0027311 A1 | 2/2005 | Wiener et al. | |
| 2006/0079874 A1 | 4/2006 | Faller et al. | |
| 2006/0095096 A1 | 5/2006 | DeBenedictis et al. | |
| 2007/0191713 A1* | 8/2007 | Eichmann | A61B 17/1606 600/471 |
| 2007/0282333 A1 | 12/2007 | Fortson et al. | |
| 2008/0097501 A1 | 4/2008 | Blier | |
| 2008/0200940 A1 | 8/2008 | Eichmann et al. | |
| 2009/0143797 A1 | 6/2009 | Smith et al. | |
| 2009/0209990 A1 | 8/2009 | Yates et al. | |
| 2010/0069940 A1 | 3/2010 | Miller et al. | |
| 2011/0015660 A1 | 1/2011 | Wiener et al. | |
| 2011/0087218 A1 | 4/2011 | Boudreaux et al. | |
| 2012/0116261 A1 | 5/2012 | Mumaw et al. | |
| 2012/0116388 A1 | 5/2012 | Houser et al. | |
| 2012/0116391 A1 | 5/2012 | Houser et al. | |

OTHER PUBLICATIONS

International Preliminary Report on Patentability dated Dec. 2, 2014 and Written Opinion dated Nov. 21, 2013 for Application No. PCT/US2013/042668.
U.S. Appl. No. 13/426,760, filed Mar. 22, 2012, Kimball et al.
U.S. Appl. No. 13/426,792, filed Mar. 22, 2012, Kimball et al.
U.S. Appl. No. 13/484,584, filed May 31, 2012, Price et al.

\* cited by examiner

SURGICAL INSTRUMENT WITH STRESS SENSOR

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through a cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient.

Examples of such endoscopic surgical instruments that may be adapted to include such user interface aides may include those disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,416,101 entitled "Motor-Driven Surgical Cutting and Fastening Instrument with Loading Force Feedback," issued Aug. 26, 2008, the disclosure of which is incorporated by reference herein; U.S. Pat. No. 7,738,971 entitled "Post-Sterilization Programming of Surgical Instruments," issued Jun. 15, 2010, the disclosure of which is incorporated by reference herein; U.S. Pub. No. 2006/0079874 entitled "Tissue Pad for Use with an Ultrasonic Surgical Instrument," published Apr. 13, 2006, the disclosure of which is incorporated by reference herein; U.S. Pub. No. 2007/0191713 entitled "Ultrasonic Device for Cutting and Coagulating," published Aug. 16, 2007, the disclosure of which is incorporated by reference herein; U.S. Pub. No. 2007/0282333 entitled "Ultrasonic Waveguide and Blade," published Dec. 6, 2007, the disclosure of which is incorporated by reference herein; U.S. Pub. No. 2008/0200940 entitled "Ultrasonic Device for Cutting and Coagulating," published Aug. 21, 2008, the disclosure of which is incorporated by reference herein; U.S. Pub. No. 2009/0209990 entitled "Motorized Surgical Cutting and Fastening Instrument Having Handle Based Power Source," published Aug. 20, 2009, now U.S. Pat. No. 8,657,174, issued Feb. 25, 2014, the disclosure of which is incorporated by reference herein; and U.S. Pub. No. 2010/0069940 entitled "Ultrasonic Device for Fingertip Control," published Mar. 18, 2010, now U.S. Pat. No. 9,023,071, issued May 5, 2015, the disclosure of which is incorporated by reference herein; U.S. Pat. Pub. No. 2011/0015660, entitled "Rotating Transducer Mount for Ultrasonic Surgical Instruments," published Jan. 20, 2011, now U.S. Pat. No. 8,461,744, issued Jun. 11, 2013, the disclosure of which is incorporated by reference herein; and U.S. Pat. Pub. No. 2011/0087218, entitled "Surgical Instrument Comprising First and Second Drive Systems Actuatable by a Common Trigger Mechanism," published Apr. 14, 2011, now U.S. Pat. No. 8,939,974, issued Jan. 27, 2015, the disclosure of which is incorporated by reference herein. Additionally, some of the foregoing surgical tools may include a cordless transducer such as that disclosed in U.S. Pat. Pub. No. 2009/0143797, entitled "Cordless Hand-held Ultrasonic Cautery Cutting Device," published Jun. 4, 2009, now U.S. Pat. No. 8,149,757, issued Apr. 16, 2013, the disclosure of which is incorporated by reference herein.

Some of the surgical instruments may be used, or adapted for use, in robotic-assisted surgery settings such as that disclosed in U.S. Pat. No. 6,783,524, entitled "Robotic Surgical Tool with Ultrasound Cauterizing and Cutting Instrument," issued Aug. 31, 2004.

While a variety of devices and methods have been made and used for endoscopic surgical procedures, it is believed that no one prior to the inventor(s) has made or used the technology described herein.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
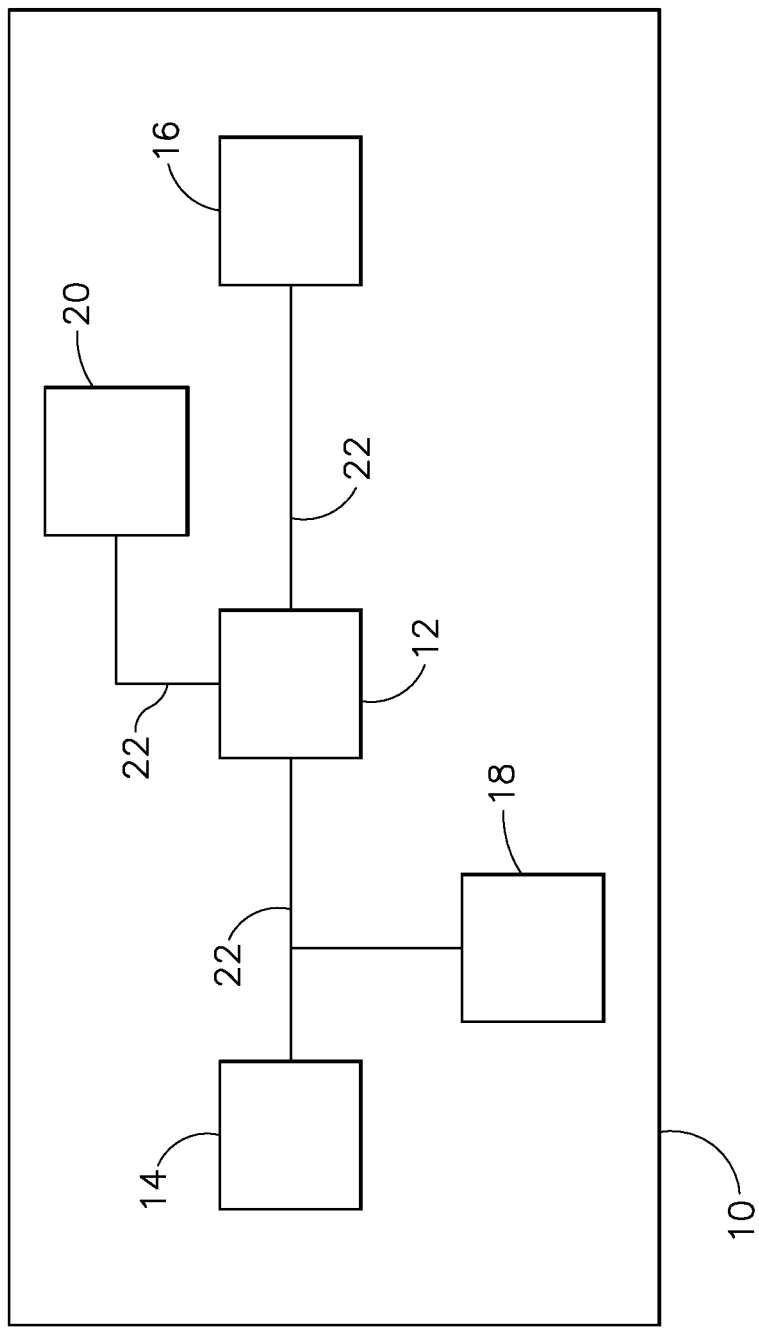
FIG. 1 depicts a block schematic of an exemplary surgical instrument having one or more sensors.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It should therefore be understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Overview

FIG. 1 shows components of an exemplary surgical instrument (10) in diagrammatic block form. As shown, surgical instrument (10) comprises a control module (12), a power source (14), and an end effector (16). In some versions, power source (14) may be an internal power source, while in others, power source (14) may be provided from an outside source. Merely exemplary internal power sources (14) may include NiMH batteries, Li-ion batteries (e.g., prismatic cell type lithium ion batteries, etc.), Ni-Cad batteries, or any other type of power source as may be apparent to one of ordinary skill in the art in light of the teachings herein. Merely exemplary external power sources (14) may include a generator, such as the GEN 300 sold by Ethicon Endo-Surgery, Inc. of Cincinnati, Ohio. Control module (12) may comprise a microprocessor, an application specific integrated circuit (ASIC), memory, a printed circuit board (PCB), a storage device (such as a solid state drive or hard disk), firmware, software, or any other suitable control module components as will be apparent to one of ordinary skill in the art in light of the teachings herein. In some versions, control module (12) further comprises EEPROM to store data thereon. For instance, the EEPROM may store machine readable code to control various components of surgical instrument (10) or the EEPROM may contain one or more operational settings and/or modes stored in data tables. Of course other machine readable code and/or configurations for the EEPROM will be apparent to one of ordinary skill in the art in view of the teachings herein. Control module (12) and power source (14) are coupled by an electrical connection (22), such as a cable and/or traces in a circuit board, etc., to transfer power from power source (14) to control module (12). Alternatively, power source (14) may be selectively coupled to control module (12). This allows power source (14) to be detached and removed from surgical instrument (10), which may further allow power source (14) to be readily recharged or reclaimed for resterilization and reuse, such as in accordance with the various teachings herein. In addition or in the alternative, control module (12) may be removed for servicing, testing, replacement, or any other purpose as will be apparent to one of ordinary skill in the art in view of the teachings herein.

End effector (16) is coupled to control module (12) by another electrical connection (22). End effector (16) is configured to perform a desired function of surgical instrument (10). By way of example only, such function may include cauterizing tissue, ablating tissue, severing tissue, ultrasonically vibrating, stapling tissue, or any other desired task for surgical instrument (10). End effector (16) may thus include an active feature such as an ultrasonic blade, a pair of clamping jaws, a sharp knife, a staple driving assembly, a monopolar RF electrode, a pair of bipolar RF electrodes, a thermal heating element, and/or various other components. End effector (16) and/or surgical instrument (10) may be further constructed in accordance with at least some of the teachings of example is described in U.S. Pat. Pub. No. 2011/0015660, entitled "Rotating Transducer Mount for Ultrasonic Surgical Instruments," published Jan. 20, 2011, now U.S. Pat. No. 8,461,744, issued Jun. 11, 2013, the disclosure of which is incorporated by reference herein; U.S. Pat. No. 7,416,101 entitled "Motor-Driven Surgical Cutting and Fastening Instrument with Loading Force Feedback," issued Aug. 26, 2008, the disclosure of which is incorporated by reference herein; and/or U.S. Pat. No. 6,500,176 entitled "Electrosurgical Systems and Techniques for Sealing Tissue," issued Dec. 31, 2002, the disclosure of which is incorporated by reference herein.

End effector (16) may also be removable from surgical instrument (10) for servicing, testing, replacement, or any other purpose as will be apparent to one of ordinary skill in the art in view of the teachings herein. In some versions, end effector (16) is modular such that surgical instrument (10) may be used with different kinds of end effectors (e.g., as taught in U.S. Non-Provisional application Ser. No. 13/269,870, entitled "Surgical Instrument with Modular Shaft and End Effector," filed Oct. 10, 2011, now U.S. Pat. No. 9,510,895, issued Dec. 6, 2016, the disclosure of which is incorporated by reference herein; U.S. patent application Ser. No. 13/484,584, entitled "Surgical Instrument with Orientation Sensing," filed on even date herewith, now U.S. Pat. No. 9,572,592, issued Feb. 21, 2017, the disclosure of which is incorporated by reference herein; and/or etc.). Various other configurations of end effector (16) may be provided for a variety of different functions depending upon the purpose of surgical instrument (10) as will be apparent to those of ordinary skill in the art in view of the teachings herein. Similarly, other types of components of a surgical instrument (10) that may receive power from power source (14) will be apparent to those of ordinary skill in the art in view of the teachings herein.

Surgical instrument (10) of the present example includes an activation feature (18), though it should be understood that such a component is merely optional. Activation feature (18) is coupled to control module (12) and power source (14) by electrical connection (22). Activation feature (18) may be configured to selectively provide power from power source (14) to end effector (16) (and/or to some other component of surgical instrument (10)) to activate surgical instrument (10) when performing a procedure. Merely exemplary activation features (18) may include a trigger, a capacitive touch sensor, a resistive touch sensor, an electromechanical button, and/or any other activation feature (18) as will be apparent to one of ordinary skill in the art in view of the teachings herein. Activation feature (18) may be further constructed in accordance with at least some of the teachings of U.S. Pat. Pub. No. 2010/0069940, entitled "Ultrasonic Device for Fingertip Control," published Mar. 18, 2010, now U.S. Pat. No. 9,023,071, issued May 5, 2015, the disclosure of which is incorporated by reference herein.

Surgical instrument (10) further includes a sensor (20). Sensor (20) is also coupled to control module (12) by an electrical connection (22) and may be configured to provide a variety of information to control module (12) during a procedure. By way of example only, such configurations may include sensing a temperature at end effector (16) or determining the oscillation rate of end effector (16). Merely exemplary temperature sensing sensors are described in U.S. Non-provisional patent application Ser. No. 13/277,328, entitled "Surgical Instrument with Sensor and Powered Control," filed Oct. 20, 2011, published as U.S. Pub. No. 2012/0116391 on May 10, 2012, the disclosure of which is incorporated by reference herein. In some versions, sensor (20) may comprise a sensor (20) operable to detect the orientation and/or movement of surgical instrument (10). For example, sensor (20) may comprise a gyroscopic sensor, an inclinometer, an accelerometer, and/or any other suitable orientation and/or movement sensor as will be apparent to one of ordinary skill in the art in view of the teachings herein. In yet a further version, sensor (20) may be configured to detect the magnitude and orientation of force on end effector (16) of surgical instrument (10). Examples of such force sensors will be described in greater detail below. In addition, or in the alternative, sensor (20) may be constructed n accordance with at least some of the teachings of U.S. patent application Ser. No. 13/484,584, entitled "Surgical Instrument with Orientation Sensing," filed on even date herewith, now U.S. Pat. No. 9,572,592, issued Feb. 21, 2017, the disclosure of which is incorporated by reference herein. Data from sensor (20) may be processed by control module (12) to manage the delivery of power to end effector (16) (e.g., in a feedback loop, etc.). Various other configurations of sensor (20) may be provided depending upon the purpose of surgical instrument (10) as will be apparent to those of ordinary skill in the art in view of the teachings herein. Of course, as with other components described herein, surgical instrument (10) may have more than one sensor (20), or sensor (20) may simply be omitted if desired. Still further configurations for surgical instrument (10) will be apparent to one of ordinary skill in the art in view of the teachings herein.

II. Exemplary Surgical System and Surgical Instrument

While the following descriptions relate to surgical instruments (10) of the ultrasonic variety, it should be understood that the features described below may be readily incorporated into a wide variety of surgical instruments (10), including, but not limited to, endocutters, graspers, cutters, staplers, clip appliers, access devices, drug/gene therapy delivery devices, and energy delivery devices using ultrasonic vibrations, RF, laser, etc., and/or any combination thereof as will be apparent to one of ordinary skill in the art in view of the teachings herein.

A. Exemplary Ultrasonic Surgical System

Figure 2:
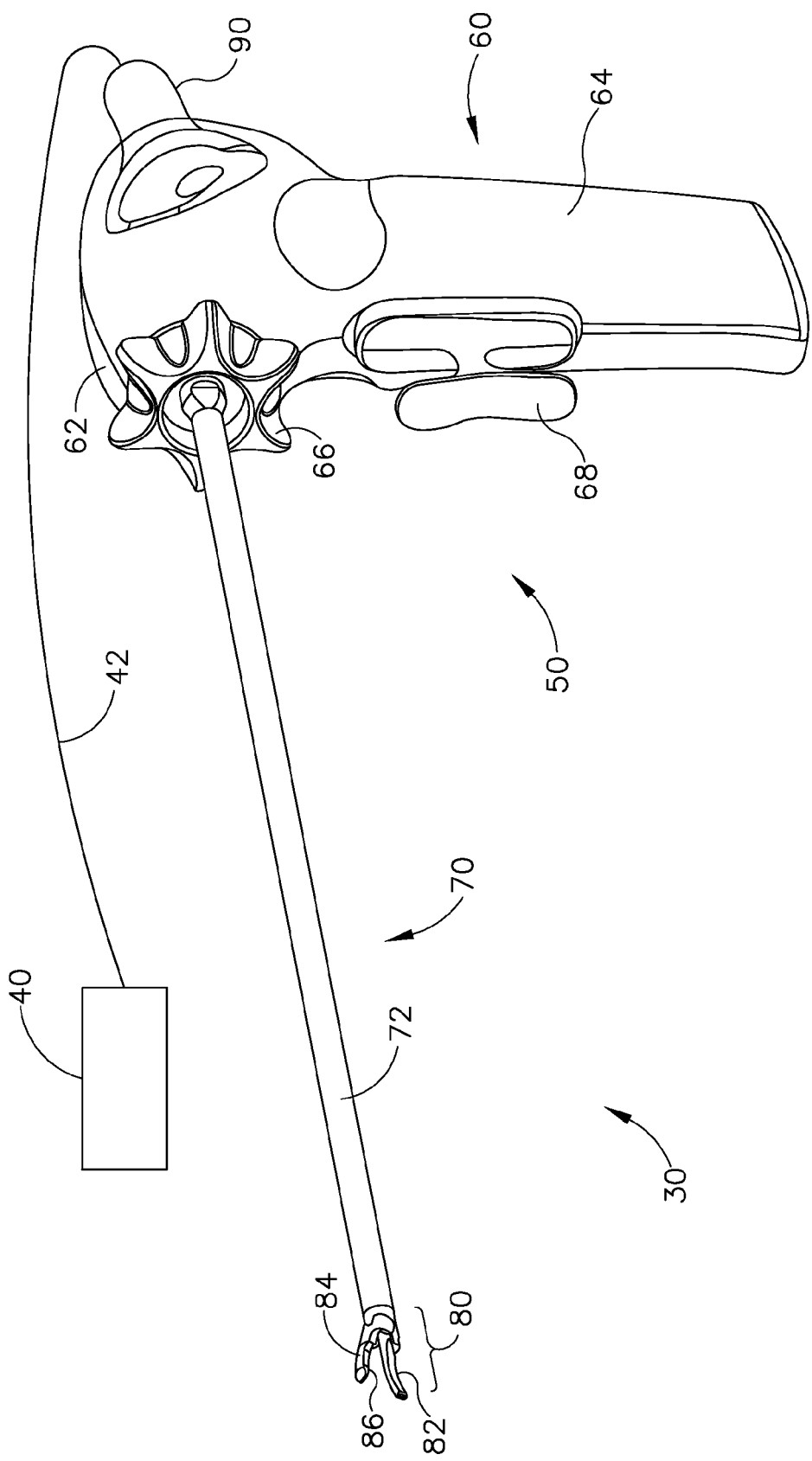
FIG. 2 depicts a perspective view of an exemplary surgical instrument.

One merely exemplary surgical system (30) having an exemplary surgical instrument (50) is shown in FIG. 2. In the present example, system (30) comprises an ultrasonic surgical instrument (50), a generator (40), and a cable (42) operable to couple generator (40) to surgical instrument (50). It should be understood that surgical instrument (50) may be viewed as an exemplary version of surgical instrument (10). A suitable generator (40) is the GEN 300 sold by Ethicon Endo-Surgery, Inc. of Cincinnati, Ohio. By way of example only, generator (40) may be constructed in accordance with the teachings of U.S. Pub. No. 2011/0087212, entitled "Surgical Generator for Ultrasonic and Electrosurgical Devices," published Apr. 14, 2011, now U.S. Pat. No. 8,986,302, issued Mar. 24, 2015, the disclosure of which is incorporated by reference herein. In some versions, generator (40) may include control module (12) described above, though this is merely optional. Moreover, while the present example is described in reference to a cable-connected surgical instrument (50), it should be understood that surgical instrument (50) may be adapted for cordless operation, such as that disclosed in U.S. Pat. Pub. No. 2009/0143797, entitled "Cordless Hand-held Ultrasonic Cautery Cutting Device," published Jun. 4, 2009, now U.S. Pat. No. 8,149,757, issued Apr. 16, 2013, the disclosure of which is incorporated by reference herein. Furthermore, surgical device (50) may also be used, or adapted for use, in robotic-assisted surgery settings such as that disclosed in U.S. Pat. No. 6,783,524, entitled "Robotic Surgical Tool with Ultrasound Cauterizing and Cutting Instrument," issued Aug. 31, 2004, the disclosure of which is incorporated by reference herein.

Surgical instrument (50) of the present example includes a multi-piece handle assembly (60), an elongated transmission assembly (70), and a transducer (90). Transmission assembly (70) is coupled to multi-piece handle assembly (60) at a proximal end of transmission assembly (70) and extends distally from multi-piece handle assembly (60). In the present example transmission assembly (70) is configured to be an elongated, thin tubular assembly for endoscopic use, but it should be understood that transmission assembly (70) may alternatively be a short assembly, such as that disclosed in U.S. Pat. Pub. No. 2007/0282333, entitled "Ultrasonic Waveguide and Blade," published Dec. 6, 2007; U.S. Pat. Pub. No. 2008/0200940, entitled "Ultrasonic Device for Cutting and Coagulating," published Aug. 21, 2008; and/or U.S. patent application Ser. No. 13/484,584, entitled "Surgical Instrument with Orientation Sensing," filed on even date herewith, now U.S. Pat. No. 9,572,592, issued Feb. 21, 2017, the disclosures of which are incorporated by reference herein. Transmission assembly (70) of the present example comprises an outer sheath (72), an inner tubular actuating member (not shown), a waveguide (not shown), and an end effector (80) located on the distal end of transmission assembly (70). In the present example, end effector (80) comprises a blade (82) coupled to the waveguide, a clamp arm (84) operable to pivot at the proximal end of transmission assembly (70), and, optionally, one or more clamp pads (86) coupleable to clamp arm (84). End effector (80) may be further configured in accordance with end effector (16) described above in reference to FIG. 1. The waveguide, which is adapted to transmit ultrasonic energy from a transducer (90) to blade (82), may be flexible, semi-flexible, or rigid. The waveguide may also be configured to amplify the mechanical vibrations transmitted through the waveguide to blade (82) as is well known in the art. The waveguide may further have features to control the gain of the longitudinal vibration along the waveguide and features to tune the waveguide to the resonant frequency of the system. One merely exemplary ultrasonic transducer (90) is Model No. HP054, sold by Ethicon Endo-Surgery, Inc. of Cincinnati, Ohio. It should also be understood that clamp arm (84) and the associated features may be constructed and operable in accordance with at least some of the teachings of U.S. Pat. No. 5,980,510, entitled "Ultrasonic Clamp Coagulator Apparatus Having Improved Clamp Arm Pivot Mount," issued Nov. 9, 1999, the disclosure of which is incorporated by reference herein. Of course clamp arm (84) may be omitted if desired.

In the present example, the distal end of the blade (82) is disposed near an anti-node in order to tune the acoustic assembly to a preferred resonant frequency $f_o$ when the acoustic assembly is not loaded by tissue. When transducer (90) is energized, the distal end of blade (82) is configured to move longitudinally in the range of, for example, approximately 10 to 500 microns peak-to-peak, and preferably in the range of about 20 to about 200 microns at a predetermined vibratory frequency $f_o$ of, for example, 55.5 kHz. When transducer (90) of the present example is activated, these mechanical oscillations are transmitted through the waveguide to end effector (80). In the present example, blade (82), being coupled to the waveguide, oscillates at the ultrasonic frequency. Thus, when tissue is secured between blade (82) and clamp arm (84), the ultrasonic oscillation of blade (82) may simultaneously sever the tissue and denature the proteins in adjacent tissue cells, thereby providing a coagulative effect with relatively little thermal spread. An electrical current may also be provided through blade (82) and clamp arm (84) to also cauterize the tissue. While some configurations for transmission assembly (70) and transducer (90) have been described, still other suitable configurations for transmission assembly (70) and transducer (90) will be apparent to one or ordinary skill in the art in view of the teachings herein.

Multi-piece handle assembly (60) of the present example comprises a mating housing portion (62) and a lower portion (64). Mating housing portion (62) is configured to receive transducer (90) at a proximal end of mating housing portion (62) and to receive the proximal end of transmission assembly (70) at a distal end of mating housing portion (62). An aperture is provided on the distal end of mating housing portion (62) for insertion of various transmission assemblies (70). A rotation knob (66) is shown in the present example to rotate transmission assembly (70) and/or transducer (90), but it should be understood that rotation knob (66) is merely optional. Mating housing portion (62) and/or transmission assembly (70) may be further constructed in accordance with at least some of the teachings of U.S. patent application Ser. No. 13/269,870, entitled "Surgical Instrument with Modular Shaft and End Effector," filed Oct. 10, 2011, now U.S. Pat. No. 9,510,895, issued Dec. 6, 2016, the disclosure of which is incorporated by reference herein. Lower portion (64) of multi-piece handle assembly (60) includes a trigger (68) and is configured to be grasped by a user using a single hand. One merely exemplary alternative configuration for lower portion (64) is depicted in FIG. 1 of U.S. Pat. Pub. No. 2011/0015660, entitled "Rotating Transducer Mount for Ultrasonic Surgical Instruments," published Jan. 20, 2011, now U.S. Pat. No. 8,461,744, issued Jun. 11, 2013, the disclosure of which is incorporated by reference herein.

In addition, while multi-piece handle assembly (60) has been described in reference to two distinct portions (62, 64), it should be understood that multi-piece handle assembly (60) may be a unitary assembly with both portions (62, 64) combined. Multi-piece handle assembly (60) may alternatively be divided into multiple discrete components, such as a separate activation portion (operable either by a user's hand or foot) and a separate mating housing portion (62). The activation portion may be operable to activate transducer (90) and may be remote from mating housing portion (62). Multi-piece handle assembly (60) may be constructed from a durable plastic (such as polycarbonate or a liquid crystal polymer), ceramics and/or metals or any other suitable material as will be apparent to one of ordinary skill in the art in view of the teachings herein. Still other configurations for multi-piece handle assembly (60) will be apparent to those of ordinary skill in the art in view of the teachings herein. For instance, instrument (50) may be operated as part of a robotic system. Other configurations for multi-piece handle assembly (60) will also be apparent to those of ordinary skill in the art in view of the teachings herein. By way of example only, surgical instrument (50) may be constructed in accordance with at least some of the teachings of U.S. Pat. Pub. No. 2006/0079874; U.S. Pat. Pub. No. 2007/0191713; U.S. Pat. Pub. No. 2007/0282333; U.S. Pat. Pub. No. 2008/0200940; U.S. Pat. Pub. No. 2011/0015660; now U.S. Pat. No. 8,461,744, issued Jun. 11, 2013; U.S. Pat. No. 6,500,176; U.S. Pat. Pub. No. 2011/0087218; and/or U.S. Pat. Pub. No. 2009/0143797, now U.S. Pat. No. 8,149,757, issued Apr. 16, 2013, the disclosures of which are incorporated by reference herein.

B. Exemplary Detachable End Effector

Figure 3:
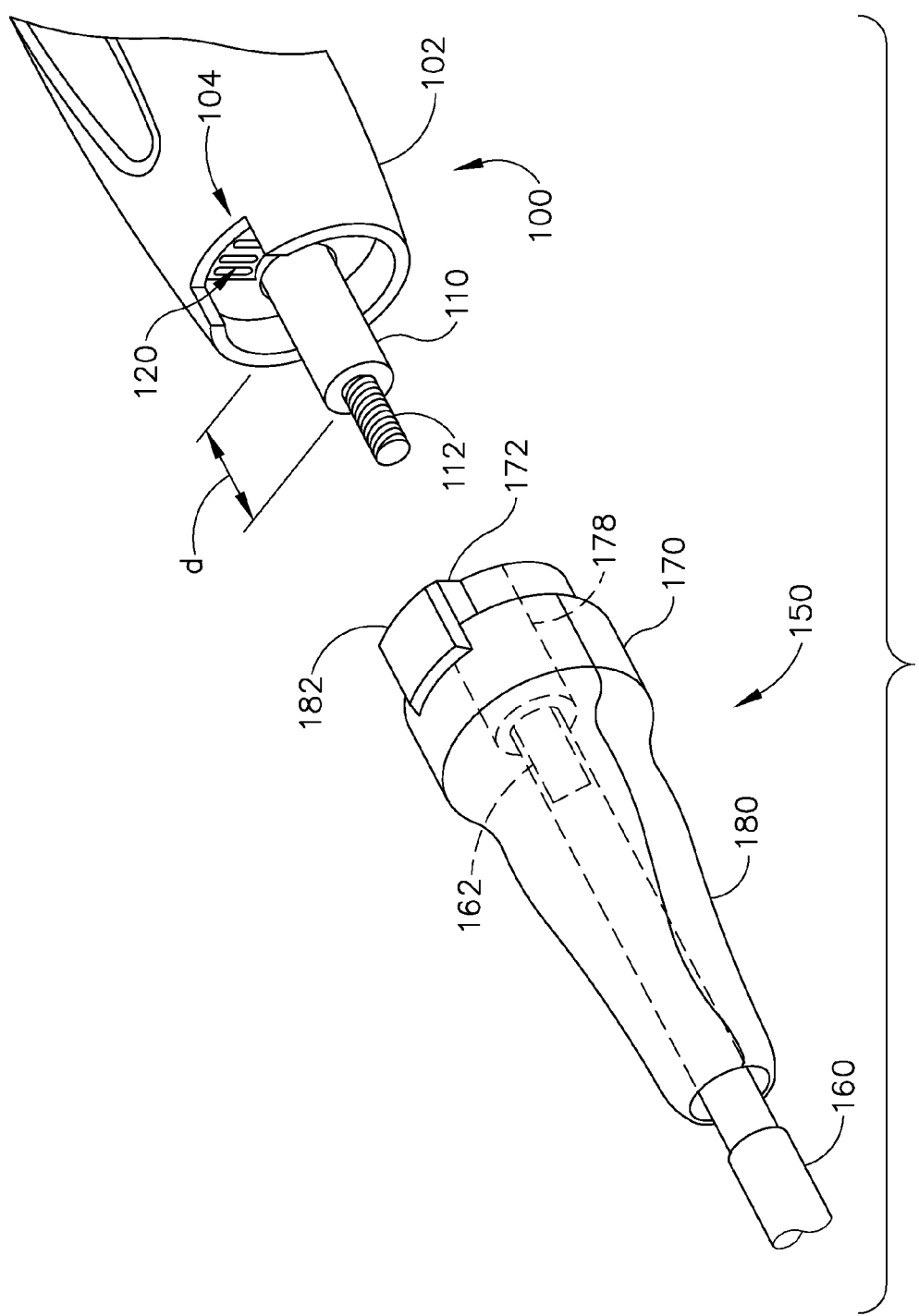
FIG. 3 depicts a partial perspective view of an exemplary surgical instrument having an exemplary detachable end effector.
Figure 4:
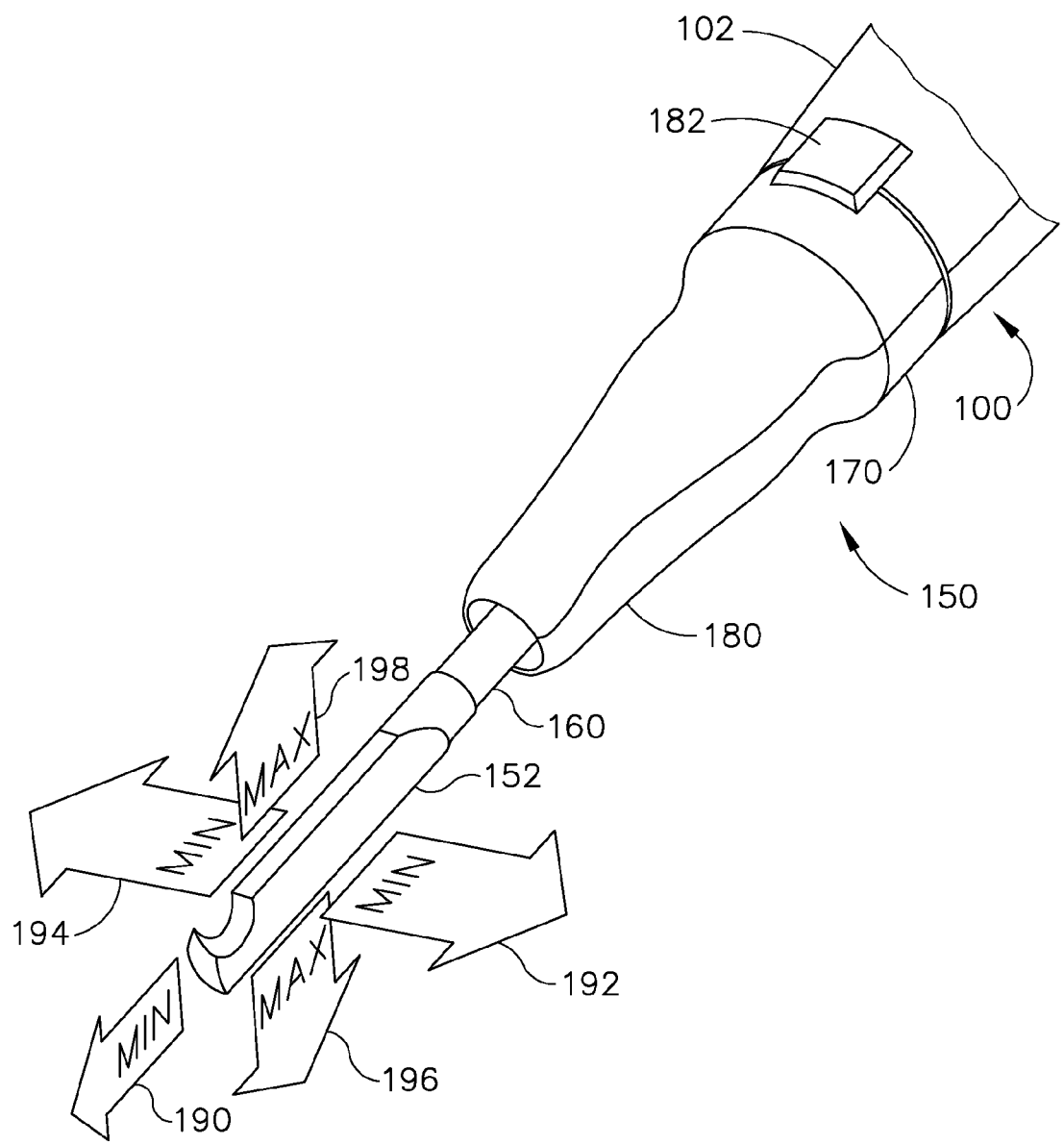
FIG. 4 depicts a partial perspective view of the end effector of FIG. 3 and various directional forces that may be applied to a blade of the end effector.

FIGS. 3-4 depict an end of an exemplary surgical instrument (100) and an exemplary detachable end effector (150). Other features of surgical instrument (100) may be configured as described above with respect to surgical instruments (10, 50). In the example shown, instrument (100) comprises a casing (102), a transducer shaft (110) extending from casing (102), and a plurality of electrical contacts (120) on casing (102). Transducer shaft (110) is configured to threadably couple to a waveguide (160) of end effector (150) such that ultrasonic vibrations from a transducer within instrument (100) can be transmitted to a blade (152) (shown in FIG. 4) of end effector (150). In the example shown, transducer shaft (110) includes a threaded portion (112) that begins at a distance d away from a distal most point of casing (102). Distance d corresponds to a longitudinal length of a keyblock (170) such that threaded portion (112) is located within rotation sleeve (180) of end effector (150) when keyblock (170) is coupled to casing (102). Accordingly, waveguide (160) can be threadably coupled to transducer shaft (110) while keyblock (170) is engaged with casing (102). Contacts (120) are metallic members that abut complementary contacts (not shown) on end effector (150) such that one or more components of end effector (150) are electrically coupled to instrument (100). In some versions, contacts (120) are further electrically coupled to a control module, such as control module (12) described above. Of course other electrical coupling features between end effector (150) and instrument (100) (e.g., inductive coupling, etc.) will be apparent to one of ordinary skill in the art in view of the teachings herein. In the present example, contacts (120) are disposed within a keyway portion (104) of casing (102) such that end effector (150) can only be coupled to casing (102) in a single orientation. Thus, keyway portion (104) can ensure that contacts (120) are aligned with the complementary contacts of end effector (150). Still further configurations for instrument (100) will be apparent to one of ordinary skill in the art in view of the teachings herein.

End effector (150) comprises waveguide (160), rotation sleeve (180), keyblock (170), and a module (182). In the present example, waveguide (160) is coupled to rotation sleeve (180) such that rotation of rotation sleeve (180) rotates waveguide (160) relative to keyblock (170). Waveguide (160) extends distally from rotation sleeve (180) and terminates at blade (152) (shown in FIG. 4). It should be understood that various features in addition, or in the alternative, to blade (152) may be included distally of rotation sleeve (180), such as one or more clamp arms. In the example shown, waveguide (160) includes a threaded portion (162) (shown in phantom) to threadably couple waveguide (160) to transducer shaft (110). Thus, when keyblock (170) is engaged with casing (102), as will be described below, rotation sleeve (180) is operable to threadably couple waveguide (160) to transducer shaft (110). Of course further coupling features for waveguide (160) and transducer shaft (110) will be apparent to one of ordinary skill in the art in view of the teachings herein. Keyblock (170) of the present example comprises a key portion (172), a central bore (178) (shown in phantom), and a module (182) mounted to keyblock (170). Central bore (178) is sized and configured to permit transducer shaft (110) to insert through keyblock (180) to engage waveguide (160), as described above. Key portion (172) is configured to insert into keyway portion (104) of casing (102) such that keyblock (170) is rotationally fixed relative to casing (102). Thus, keyblock (170) provides a mechanical ground for rotation sleeve (180) when keyblock (170) is engaged with casing (102). Key portion (172) further includes complementary contacts to contacts (120) described above. The engagement of key portion (172) with keyway portion (104) is configured to rotationally align the set of contacts such that when keyblock (170) is engaged with casing (102), the set of contacts are electrically coupled. The complementary contacts are coupled to module (182) such that module (182) is electrically coupled to contacts (120) when end effector (150) is coupled to instrument (100).

In the present example, module (182) comprises a non-volatile solid state memory module that is operable to store one or more configuration datas. For example, module (182) may contain a configuration data regarding the type and characteristic properties of end effector (150) to be used by a control module, such as control module (12) described in reference to FIG. 1, of surgical instrument (100). By way of example only, the configuration data may include properties such as blade length, blade material, blade geometry, waveguide geometry, waveguide material, natural damping characteristics, natural frequencies, mean time to failure (MTTF), etc. Such properties may be used by the control module when determining a corrective action, determining energy settings for instrument (100), and/or otherwise, as will be described in greater detail below. Of course it should be understood that other components may be included with, integrated into, and/or substituted for module (182). For example, various sensors such as accelerometers, gyroscopes, temperature sensors, force sensors, etc. may be included with, integrated into, and/or substituted for module (182). End effector (150) may be further constructed in accordance with at least some of the teachings of U.S. patent application Ser. No. 13/484,584, entitled "Surgical Instrument with Orientation Sensing," filed on even date herewith, now U.S. Pat. No. 9,572,592, issued Feb. 21, 2017, the disclosure of which are incorporated by reference herein. Still further configurations for module (182), end effector (150), and/or instrument (100) will be apparent to one of ordinary skill in the art in view of the teachings herein.

Referring now to FIG. 4, a set of directional arrows (190, 192, 194, 196, 198) are shown disposed about blade (152). Arrow (190) corresponds to the longitudinal axis of blade (152) and waveguide (160). Arrows (192, 194) correspond to the lateral axis relative to blade (152). Arrows (196, 198) correspond to the vertical axis relative to blade (152). In the present example, arrows (190, 192, 194, 196, 198) correspond to the direction blade (152) is pressed against tissue when a user is using instrument (100) in a surgical procedure. By way of example only, in some instances it may be preferable to activate the transducer at a low energy setting when blade (152) is pressed against tissue in the direction of arrows (190, 192, 194) and to activate the transducer at a high energy setting when blade (152) is pressed against tissue in the direction of arrows (196, 198). For example, a user may prefer to use the side and/or tip of blade (152) to coagulate, while using the upper or lower edges of blade (152) to cut through tissue. Of course it should be understood that the foregoing is merely exemplary and any energy setting may correspond with any direction of blade (152). In the present example, such energy settings and directions may be included in configuration data of module (182) to be used by the control module and/or may be provided through other means to the control module. Such settings may vary based on any number of factors, including, but not limited to, the features and/or geometry of blade (152) and/or other parts of end effector (150), the surgical procedure in which end effector (150) will be used, the individual user's preferences, and/or other factors. The use of such energy settings will be described in greater detail below in reference to FIG. 21.

III. Exemplary Active Damping Assemblies and Directional Force Sensors

In some instances, it may be useful to actively control the energy setting of transducer (90) and/or other components in surgical instrument (10, 50, 100). For instance, if a transverse motion occurs in waveguide (160) and/or other portion of the ultrasonic drive train of surgical instrument (10, 50, 100) during a surgical procedure, the transverse motion may disrupt or otherwise interfere with the oscillatory motion from transducer (90). In addition, in some cases the transverse motion may induce an unstable mode of vibration, thereby potentially damaging instrument (10, 50, 100). Some instruments (10, 50, 100) may include an FEP such as a polymeric sheath or extrusion (e.g., a perflorinated polymer with high temperature stability) that is applied to the waveguide (160) in predetermined locations to dampen deleterious or otherwise undesirable transverse modes. Elimination or reduction of transverse motions during the use of surgical instrument (10, 50, 100) may permit larger manufacturing tolerances and/or eliminate the need for FEP. In other instances, it may be useful to actively control the energy setting of transducer (90) in order to adapt the energy setting in response to how the user is using instrument (10, 50, 100). For instance, as noted above, the direction in which blade (82, 152) is pressed against tissue may be used as input to control module (12) to dynamically adjust the energy setting for transducer (90) in real time during the surgical procedure, such that the user need not select any particular energy level. Accordingly, various active damping assemblies and/or directional force sensors that may be incorporated into various surgical instruments (10, 50, 100), including, but not limited to ultrasonic instruments, will now be described, while other examples will be apparent to those of ordinary skill in the art in view of the teachings herein.

A. Handle Assembly Mounted Active Damping Assembly

Figure 5:
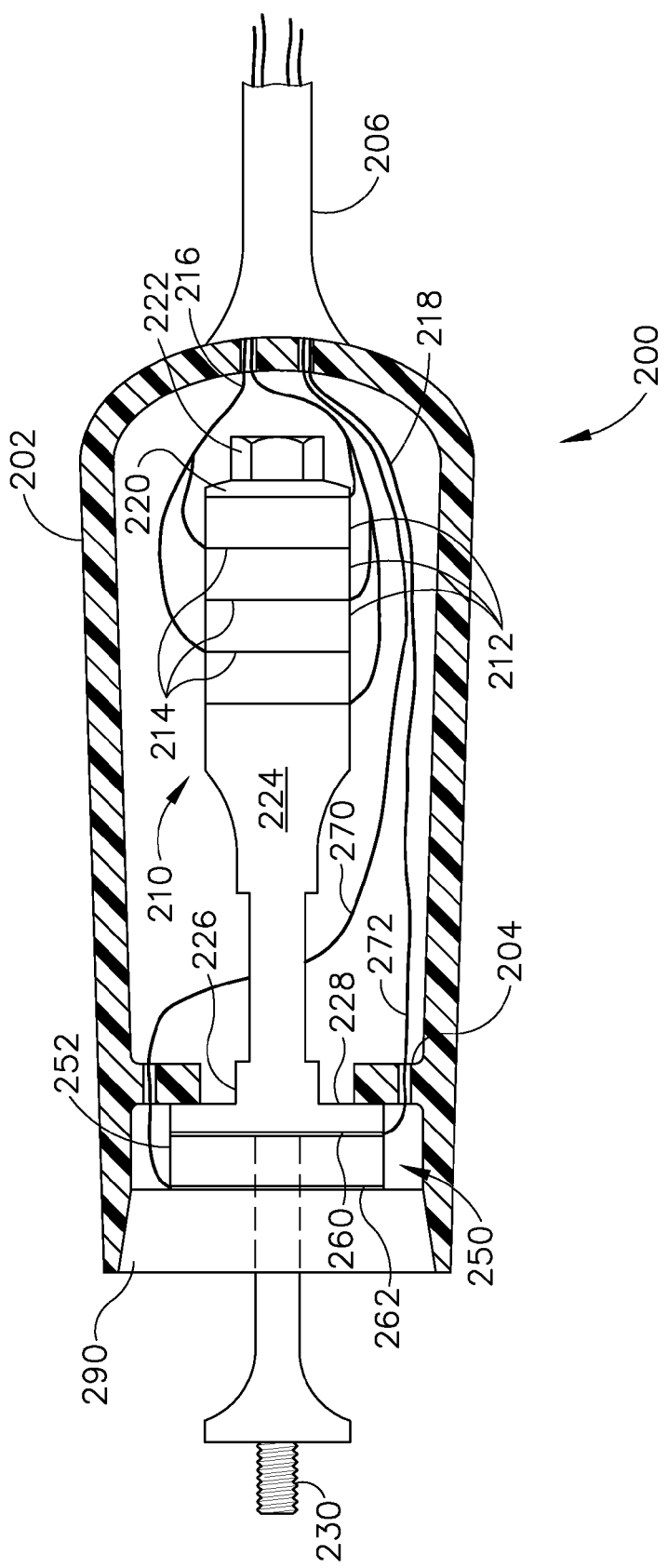
FIG. 5 depicts a side elevation view of an exemplary handle assembly having a portion of a casing removed to show an exemplary transducer and distal piezoelectric disc assembly.

FIG. 5 depicts an exemplary handle assembly (200) comprising a casing (202), a transducer (210), a distal piezoelectric disc assembly (250), and a nosecone (290). Casing (202) of the present example is sized and configured to contain transducer (210) and other components (not shown) therein. Casing (202) may be constructed from a durable plastic (such as polycarbonate or a liquid crystal polymer), ceramics and/or metals or any other suitable material as will be apparent to one of ordinary skill in the art in view of the teachings herein. As shown in FIG. 5, casing (202) includes an interior annular flange (204) configured to engage a transducer flange (226), as will be described below, to provide a mechanical ground between casing (202) and transducer (210). Casing (202) further includes a proximally extending cable (206) that carries a plurality of wires (216, 218, 270, 272) to a power source, such as generator (40) described above. Of course, in some versions cable (206) may be omitted and the power source may be located within casing (202). Casing (202) may be further constructed in accordance with at least some of the teachings of multi-piece handle assembly (60) described above. Nose cone (290) is mechanically fixed to a distal end of casing (202) to compress distal piezoelectric disc assembly (250) between nosecone (290) and a transducer flange (226), as will be described below.

Transducer (210) comprises a plurality of piezoelectric elements (212) having alternating electrodes (214) disposed between successive piezoelectric elements (212) to form a stack of piezoelectric elements. Piezoelectric elements (212) may be fabricated from any suitable material, for example, lead zirconate-titanate, lead meta-niobate, lead titanate, and/or any suitable piezoelectric crystal material between electrodes (214). In the present example, alternating electrodes (214) are electrically coupled via wires (216, 218) such that a voltage potential is formed across the plurality of piezoelectric elements (212) when a power supply is coupled to wires (216, 218). Accordingly, when the power supply is activated, the plurality of piezoelectric elements (212) converts the electrical power into ultrasonic vibrations. Such ultrasonic vibrations are transmitted distally to a waveguide (not shown) via a distal resonator (224) and a threaded portion (230) that couples the waveguide to distal resonator (224). At a proximal end of the stack of piezoelectric elements (212) is a proximal resonator (220). A bolt (222) is inserted through annular openings (not shown) in proximal resonator (220) and the stack of piezoelectric elements (212) and couples to distal resonator (224). Accordingly, bolt (222), proximal resonator (220), the stack of piezoelectric elements (212) and electrodes (214), and distal resonator (224) substantially form transducer (210). In the present example, a transducer flange (226) is coupled to distal resonator (224) and is configured to have a proximal surface (228) abut against interior annular flange (204) of casing (202). Accordingly, the interface of transducer flange (226) and interior annular flange (204) prevents transducer (210) from moving proximally relative to casing (202). Distal resonator (224) extends distally through distal piezoelectric disc assembly (250) and terminates at threaded portion (230). Threaded portion (230) is configured to threadably couple to a waveguide, blade, and/or end effector, such as waveguide (160), blade (152), and/or end effector (150) described above. Accordingly, the ultrasonic vibrations can be transmitted from transducer (210) to the waveguide, blade, and/or end effector. Threaded portion (230) may be located at a node, an anti-node, and/or any other point along distal resonator (224). Transducer (210) may be further constructed in accordance with at least some of the teachings of U.S. patent application Ser. No. 13/274,480, entitled "Surgical Instrument with Slip Ring Assembly to Power Ultrasonic Transducer," filed Oct. 17, 2011, published as U.S. Pub. No. 2012/0116261 on May 10, 2012, the disclosure of which is incorporated by reference herein. Still other configurations for transducer (210) will be apparent to one of ordinary skill in the art in view of the teachings herein.

Distal piezoelectric disc assembly (250) is interposed between nosecone (290) and transducer flange (226). Distal piezoelectric disc assembly (250) comprises a piezoelectric disc (252) interposed between a pair of electrodes (260, 262). In the present example, distal piezoelectric disc assembly (250) comprises a single unitary piezoelectric element, though, as will be discussed in greater detail below, in some versions, distal piezoelectric disc assembly (250) may comprise a multi-piece piezoelectric element having one or more segments for detecting vibration of distal resonator (224) and one or more segments for active damping. Of course, it should be understood that, in some versions, distal piezoelectric disc assembly (250) may be used to induce one or more vibratory modes. As with piezoelectric elements (212) discussed above, piezoelectric disc (252) may be fabricated from any suitable material, for example, lead zirconate-titanate, lead meta-niobate, lead titanate, and/or any suitable piezoelectric crystal material. Electrodes (260, 262) comprise metallic members disposed on either side of piezoelectric disc (252).

Electrodes (260, 262) are coupled to wires (270, 272) such that a voltage potential is formed across piezoelectric disc (252) when a power supply is coupled to wires (270, 272). Accordingly, piezoelectric disc (252) expands or contracts depending upon the voltage potential applied across piezoelectric disc (252), thereby expanding or contracting between nosecone (290) and transducer flange (226). Thus, the motion of distal piezoelectric disc assembly (250) may be used to affect the vibrations present in distal resonator (224). In addition, or in the alternative, wires (270, 272) may be coupled to a voltage detection device (not shown). The voltage detection device may be within the end effector, within handle assembly (200), and/or within the power supply. In some versions, the voltage detection device may be integrated into a control module, such as control module (12). When a compression or expansion force is applied to distal piezoelectric disc assembly (250), the compression or expansion of piezoelectric disc (252) generates a voltage that can be detected by the voltage detection device. Accordingly, the vibrations within distal resonator (224) can be measured. Of course it should be understood that more than one distal piezoelectric disc assembly (250) may be provided. For instance, a first distal piezoelectric disc assembly (250) may be used for active damping and a second distal piezoelectric disc assembly (250) may be used for detecting vibrations. Still further configurations and/or constructions for exemplary handle assembly (200) and/or distal piezoelectric disc assembly (250) will be apparent to one of ordinary skill in the art in view of the teachings herein. By way of example only, in some versions, distal piezoelectric disc assembly (250) may be omitted and a voltage sensitive membrane and/or other force sensor, such as a strain gauge, may be used in instances where a measurement of the magnitude and/or direction of force is needed without active damping capabilities.

B. End Effector Mounted Active Damping Assembly

Figure 6:
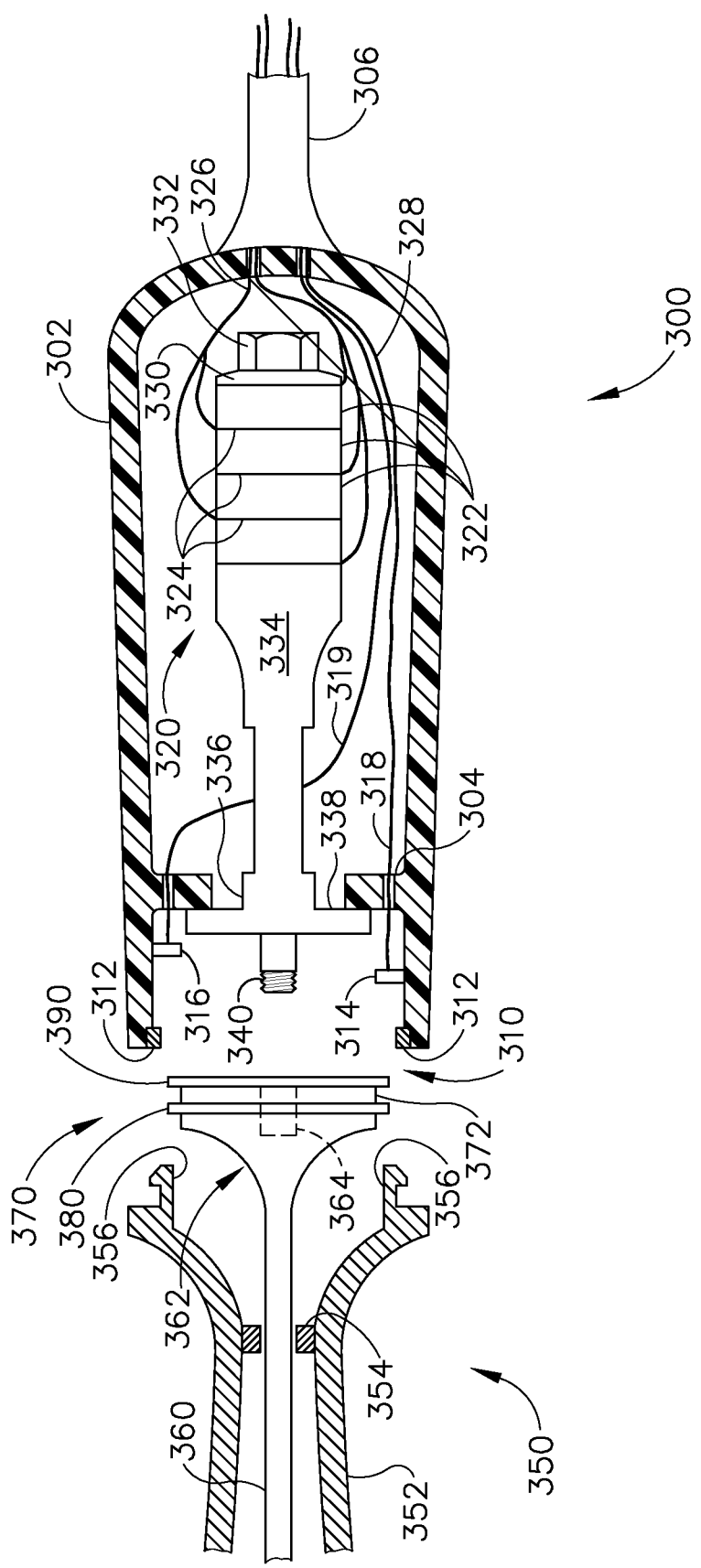
FIG. 6 depicts a side elevation view of an exemplary alternative handle assembly and detachable end effector having portions of the respective casings removed and showing an exemplary alternative distal piezoelectric disc assembly coupled to the end effector.

FIG. 6 depicts an exemplary alternative handle assembly (300) and a detachable end effector (350). Handle assembly (300) comprises a casing (302) and a transducer (320). Casing (302) of the present example is sized and configured to contain transducer (320) and other components (not shown) therein. Casing (302) may be constructed from a durable plastic (such as polycarbonate or a liquid crystal polymer), ceramics and/or metals or any other suitable material as will be apparent to one of ordinary skill in the art in view of the teachings herein. As shown in FIG. 6, casing (302) includes an interior annular flange (304) configured to engage a transducer flange (336), as will be described below, to provide a mechanical ground between casing (302) and transducer (320). Casing (302) also includes a proximally extending cable (306) that carries a plurality of wires (318, 319, 326, 328) to a power source, such as generator (40) described above. Of course, in some versions cable (306) may be omitted and the power source may be located within casing (302).

Casing (302) also includes an open distal end (310) and a pair of tabs (312) configured to engage with and secure a pair of snaps (356) from end effector (350). In the present example, a pair of contacts (314, 316) are positioned within open distal end (310) such that contacts (314, 316) are selectively electrically coupled to a pair of electrodes (380, 390), respectively, of a piezoelectric disc assembly (370), as will be described below in more detail. Contacts (314, 316) in the present example comprise resiliently biased leaf-spring contacts, though other resiliently biased contacts or other contacts may be provided as well. In some versions, spring-loaded ball bearings may be used to electrically couple to electrodes (380, 390). Still other features for rotatably coupling to electrodes (380, 390) are described in U.S. patent application Ser. No. 13/269,870, entitled "Surgical Instrument with Modular Shaft and End Effector," filed Oct. 10, 2011, now U.S. Pat. No. 9,510,985, issued Dec. 6, 2016,the disclosure of which is incorporated by reference herein. Contacts (314, 316) are coupled to wires (318, 319), respectively. Wires (318, 319) may then be coupled to a power assembly, such as generator (40) describe above, and/or to a voltage detection device (not shown). Casing (302) may be further constructed in accordance with at least some of the teachings of multi-piece handle assembly (60) described above.

Transducer (320) comprises a plurality of piezoelectric elements (322) having alternating electrodes (324) disposed between successive piezoelectric elements (322) to form a stack of piezoelectric elements. Piezoelectric elements (322) may be fabricated from any suitable material, for example, lead zirconate-titanate, lead meta-niobate, lead titanate, and/or any suitable piezoelectric crystal material between electrodes (324). In the present example, alternating electrodes (324) are electrically coupled via wires (326, 328) such that a voltage potential is formed across the plurality of piezoelectric elements (322) when a power supply is coupled to wires (326, 328). Accordingly, when the power supply is activated, the plurality of piezoelectric elements (322) converts the electrical power into ultrasonic vibrations. Such ultrasonic vibrations are transmitted distally to a waveguide (360) of end effector (350) when waveguide (360) is threadably coupled transducer (320). At a proximal end of the stack of piezoelectric elements (322) is a proximal resonator (330). A bolt (332) is inserted through annular openings (not shown) in proximal resonator (330) and the stack of piezoelectric elements (322) and couples to a distal resonator (334). Accordingly, bolt (332), proximal resonator (330), the stack of piezoelectric elements (322) and electrodes (324), and distal resonator (334) substantially form transducer (320). In the present example, a transducer flange (336) is coupled to distal resonator (334) at a distal end of distal resonator (334) and is configured to have a proximal surface (338) abut against interior annular flange (304) of casing (302). Accordingly, the interface of transducer flange (336) and interior annular flange (304) prevents transducer (320) from moving proximally relative to casing (302). A threaded portion (340) is configured to threadably couple to waveguide (360) of end effector (350). Threaded portion (340) may be located at a node, an anti-node, and/or any other point along distal resonator (334). Transducer (320) may be further constructed in accordance with at least some of the teachings of U.S. patent application Ser. No. 13/274,480, entitled "Surgical Instrument with Slip Ring Assembly to Power Ultrasonic Transducer," filed Oct. 17, 2011, published as U.S. Pub. No. 2012/0116261 on May 10, 2012. the disclosure of which is incorporated by reference herein. Still other configurations for transducer (320) will be apparent to one of ordinary skill in the art in view of the teachings herein.

End effector (350) comprises a casing (352), a waveguide (360) rotatably mounted within casing (352), and a piezoelectric disc assembly (370) mounted to a proximal bell portion (362) of waveguide (360). Casing (352) includes a bushing (354) to support waveguide (360) while still permitting waveguide (360) to rotate and vibrate relative to casing (352). Of course it should be understood that other rotatable couplings may be provided, such as bearings, or, in some versions, bushing (354) may be omitted. Casing (352) further includes a pair of snaps (356) configured to engage with tabs (312) to couple end effector (350) to handle assembly (300). Of course other coupling features for coupling end effector (350) to handle assembly (300) will be apparent to one of ordinary skill in the art in view of the teachings herein. Waveguide (360) extends distally and is coupled to a blade (not shown), such as blade (82). Proximal bell portion (362) is located at a proximal end of waveguide (360) and includes a threaded recess (364) (shown in phantom) configured to threadably couple to threaded portion (340) of distal resonator (334) of transducer (320). A proximal face of proximal bell portion (362) is sized have a diameter that substantially corresponds to the diameter of piezoelectric disc assembly (370). Still other configurations for casing (352) and/or waveguide (360) will be apparent to one of ordinary skill in the art in view of the teachings herein.

Piezoelectric disc assembly (370) comprises a piezoelectric disc (372) interposed between a pair of electrodes (380, 390). In the present example, piezoelectric disc assembly (370) comprises a single unitary piezoelectric element, though, as will be discussed in greater detail below, in some versions, piezoelectric disc assembly (370) may comprise a multi-piece piezoelectric element having one or more segments for detecting vibration of distal resonator (334) and/or waveguide (360) and one or more segments for active damping. Of course, it should be understood that, in some versions, piezoelectric disc assembly (370) may be used to induce one or more vibratory modes. As with piezoelectric elements (322) discussed above, piezoelectric disc (372) may be fabricated from any suitable material, for example, lead zirconate-titanate, lead meta-niobate, lead titanate, and/or any suitable piezoelectric crystal material.

Electrodes (380, 390) comprise metallic members disposed on either side of piezoelectric disc (372). Electrodes (380, 390) are configured to electrically couple to contacts (314, 316), respectively, when end effector (350) is coupled to handle assembly (300). In the present example, an outer perimeter of each electrode (380, 390) extends outwardly from piezoelectric disc (372) such that electrodes (380, 390) interface with contacts (314, 316) in a similar manner to a slip ring assembly without piezoelectric disc (372) interfacing with contacts (314, 316). When a power supply is coupled to wires (318, 319) a voltage potential is formed across piezoelectric disc (372). Accordingly, piezoelectric disc (372) expands or contracts depending upon the voltage potential applied across piezoelectric disc (372), thereby expanding or contracting between proximal bell portion (362) and transducer flange (336). Thus, the motion of piezoelectric disc assembly (370) may be used to affect the vibrations present in distal resonator (334) and/or waveguide (360). As noted above, wires (318, 319) may be coupled to a voltage detection device (not shown). The voltage detection device may be within end effector (350), within handle assembly (300), and/or within the power supply. In some versions, the voltage detection device may be integrated into a control module, such as control module (12). When a compression or expansion force is applied to piezoelectric disc assembly (370), the compression or expansion of piezoelectric disc (372) generates a voltage that can be detected by the voltage detection device. Accordingly, the vibrations within distal resonator (334) and/or waveguide (360) can be measured. Of course it should be understood that more than one piezoelectric disc assembly (370) may be provided, for instance, a pair of stacked piezoelectric disc assemblies (370) with one piezoelectric disc assembly (370) for active damping and a second piezoelectric disc assembly (370) for detecting vibrations. Still further configurations and/or constructions for exemplary handle assembly (300), end effector (350) and/or piezoelectric disc assembly (370) will be apparent to one of ordinary skill in the art in view of the teachings herein. By way of example only, in some versions, piezoelectric disc assembly (370) may be omitted and a voltage sensitive membrane and/or other force sensor, such as a strain gauge, may be coupled to transducer flange (336) and used in instances where a measurement of the magnitude and/or direction of force is needed without active damping capabilities.

C. Exemplary Multi-Piece Piezoelectric Element

Figure 7:
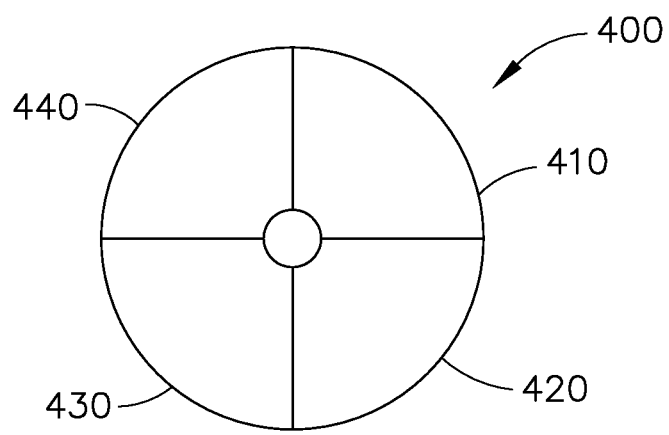
FIG. 7 depicts a front elevation view of an exemplary multi-piece piezoelectric disc assembly.

FIG. 7 depicts an exemplary multi-piece piezoelectric element (400) that may be incorporated into the foregoing piezoelectric disc assemblies (250, 370). In the present example, multi-piece piezoelectric element (400) is constructed in substantial accordance with piezoelectric disc assemblies (250, 370) described above, except that multi-piece piezoelectric element (400) is subdivided into four segments (410, 420, 430, 440). Each segment (410, 420, 430, 440) comprises a pair of electrodes and a piezoelectric element disposed between the pair of electrodes. Opposing segments (410, 430) of the present example comprise piezoelectric segments operable to drive vibration of a waveguide to counter a transverse motion. The other opposing segments (420, 440) are configured to sense the vibration from the waveguide. Accordingly, a single multi-piece piezoelectric element (400) may be used to both sense vibrations from the waveguide and induce vibrations in the waveguide to counter a transverse motion.

Figure 8:
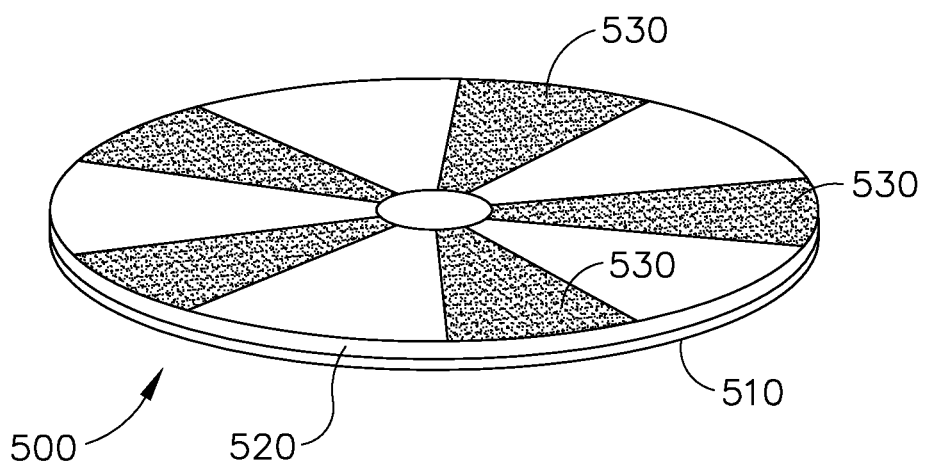
FIG. 8 depicts a perspective view of an exemplary alternative distal piezoelectric disc assembly having alternating segmented electrodes.

In some versions, driving segments (410, 430) may be operated in unison to drive or adjust the vibration of the waveguide. In other versions, driving segments (410, 430) may be driven at separate time periods and/or rates Likewise, in some versions sensing segments (420, 440) may sense the vibrations from the waveguide at the same time, while in other versions sensing segments (420, 440) may alternate the sensing of the vibrations of the waveguide or otherwise operate individually. In yet a further configuration, segments (410, 420, 430, 440) may alternate between sensing and driving vibrations. Such alternate sensing and driving of vibrations may be done by individual segments, in tandems, or as an entire group. It should be understood that the division of segments (410, 420, 430, 440) into four segments is merely optional. In some versions two or three segments may be used. In other versions, more than four segments may be used. For instance, eight or sixteen segments may be provided in some versions. It should be understood that, in the present example, segments (410, 420, 430, 440) are also operable to resolve both the magnitude and the direction of the force relative to a surgical instrument, such as surgical instruments (10, 50, 100), when segments (410, 420, 430, 440) are used to sense the vibrations from the waveguide or other ultrasonic drive train component. For instance, segments (410, 420, 430, 440) can determine a force vector encountered by a blade bearing against tissue. Of course still other configurations for multi-piece piezoelectric element (400) will be apparent to one of ordinary skill in the art in view of the teachings herein. One merely exemplary alternative configuration for a multi-piece piezoelectric element (500) is shown in FIG. 8 having a single continuous bottom electrode (510), a piezoelectric disc (520), and a plurality of segmented top electrodes (530).

In the foregoing multi-piece piezoelectric elements (400, 500), it should be understood that monitoring of the voltage changes across the various segments (410, 420, 430, 440, 530) can be used to resolve the force on the various blade surfaces, the position of the force on the blade, and/or the surgeon's actions. It should also be understood that transverse modes may excite one or more disc segments (410,

420, 430, 440, 530) along a direction that is transverse to the axis of the waveguide; and that the segment 410, 420, 430, 440, 530) detecting the transverse mode (and/or one or more other segments) may be excited to actively dampen the transverse mode. Piezoelectric discs may be fabricated in various different ways to provide a segmented performance. For instance, a homogenous piezo disc may include segmented electrode surfaces. The separation between electrode surfaces may be configured to prevent voltage breakdown at the highest intended operating voltage level. As another merely illustrative example, several discretely formed pie shaped segments may be arranged to abut each other or may be separated by air or a solid dielectric, etc. As yet another merely illustrative example, a piezo actuator may be formed as a tube or cylinder. The inner radius surfaces and the outer radius surfaces may include electrodes, and the piezo actuator may be polarized to respond longitudinally (perpendicular to the voltage gradient). In this form the outer electrode may be segmented into strips in the longitudinal direction and the center electrode (e.g., ground) may be continuous around the inner radius. Other suitable ways in which segmented element features may be provided will be apparent to those of ordinary skill in the art in view of the teachings herein.

D. Finger-Based Directional Force Sensor Assembly

Figure 9:
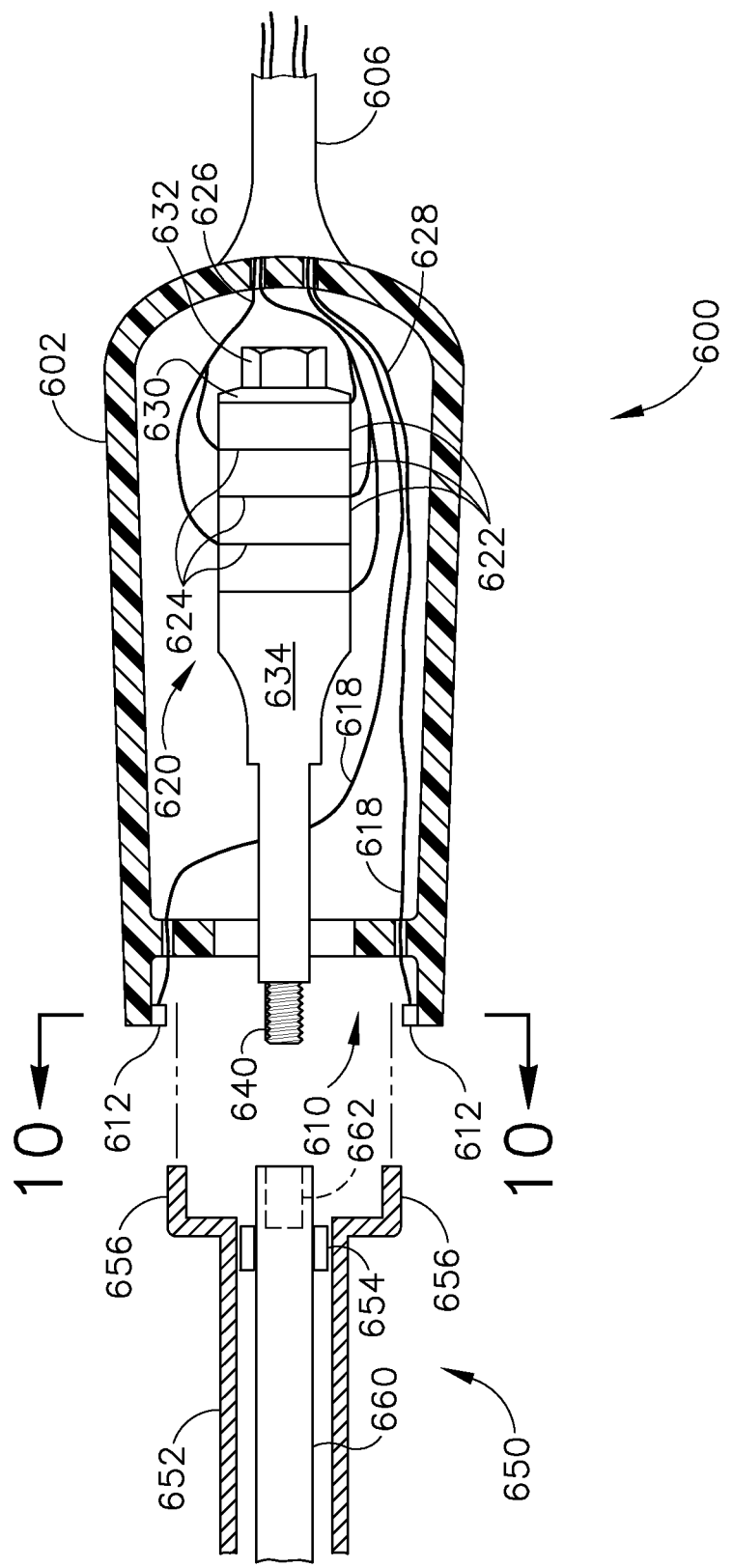
FIG. 9 depicts a side elevation view of yet another exemplary alternative handle assembly and detachable end effector having portions of the respective casings removed and showing an exemplary directional force sensor assembly.
Figure 10:
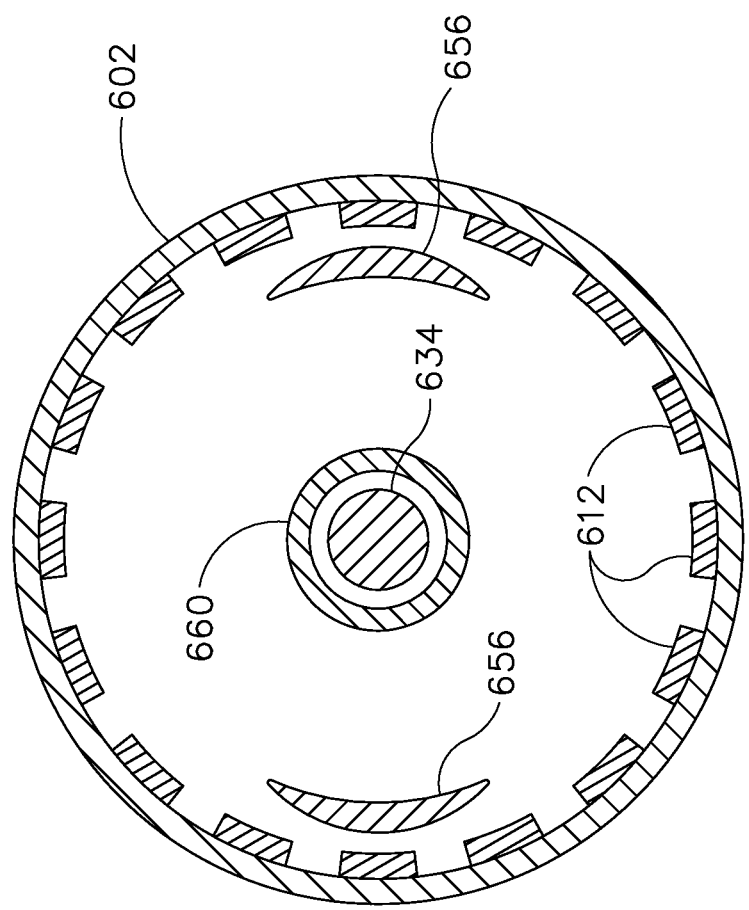
FIG. 10 depicts a cross-sectional view of the finger-based orientation and force sensor assembly of FIG. 9 taken along section line 10-10 shown in FIG. 9 when the end effector is attached.

FIGS. 9-10 depict an exemplary alternative directional force sensor assembly comprising a handle assembly (600) having a ring of piezoresistive elements (612) and an end effector (650) having a pair of fingers (656) configured to engage the piezoresistive elements (612) when end effector (650) is coupled to handle assembly (600) and a force is applied to a blade (not shown) of end effector (650). Handle assembly (600) of the present example comprises a casing (602) and a transducer (620). Casing (602) of the present example is sized and configured to contain transducer (620) and other components (not shown) therein. Casing (602) may be constructed from a durable plastic (such as polycarbonate or a liquid crystal polymer), ceramics and/or metals or any other suitable material as will be apparent to one of ordinary skill in the art in view of the teachings herein. Casing (602) includes a proximally extending cable (606) that carries a plurality of wires (618, 626, 628) to a power source, such as generator (40) described above. Of course, in some versions cable (606) may be omitted and the power source may be located within casing (602). Casing (602) also includes an open distal end (610) and a ring of piezoresistive elements (612) positioned in a ring about the interior of open distal end (610), as best seen in FIG. 10. Piezoresistive elements (612) will be described in greater detail below. Casing (602) may be further constructed in accordance with at least some of the teachings of multi-piece handle assembly (60) described above.

Transducer (620) comprises a plurality of piezoelectric elements (622) having alternating electrodes (624) disposed between successive piezoelectric elements (622) to form a stack of piezoelectric elements. In the present example, alternating electrodes (624) are electrically coupled via wires (626, 628) such that a voltage potential is formed across the plurality of piezoelectric elements (622) when a power supply is coupled to wires (626, 628). Accordingly, when the power supply is activated, the plurality of piezoelectric elements (622) converts the electrical power into ultrasonic vibrations. Such ultrasonic vibrations are transmitted distally to a waveguide (660) of end effector (650) when waveguide (660) is threadably coupled transducer (620). At a proximal end of the stack of piezoelectric elements (622) is a proximal resonator (630). A bolt (632) is inserted through annular openings (not shown) in proximal resonator (630) and the stack of piezoelectric elements (622) and couples to a distal resonator (634). Accordingly, bolt (632), proximal resonator (630), the stack of piezoelectric elements (622) and electrodes (624), and distal resonator (634) substantially form transducer (620). A threaded portion (640) of distal resonator (634) is configured to threadably couple to waveguide (660) of end effector (650). Threaded portion (640) may be located at a node, an anti-node, and/or any other point along distal resonator (634). Transducer (620) may be further constructed in accordance with at least some of the teachings of transducers (210, 320) and/or of U.S. patent application Ser. No. 13/274,480, entitled "Surgical Instrument with Slip Ring Assembly to Power Ultrasonic Transducer," filed Oct. 17, 2011, published as U.S. Pub. No. 2012/0116261 on May 10, 2012, the disclosure of which is incorporated by reference herein. Still other configurations for transducer (620) will be apparent to one of ordinary skill in the art in view of the teachings herein.

In the present example, each piezoresistive element (612) is coupled to a corresponding wire (618) that is further coupled to a voltage detection device (not shown). Accordingly, if a piezoresistive element (612) experiences a force upon it, such as a finger (656) contacting piezoresistive element (612), the voltage detection device indicates a change in voltage from the corresponding piezoresistive element (612). Such a change in voltage may be used to indicate both the magnitude of force applied to the blade of end effector (650) and the direction of the force based upon which piezoresistive element(s) (612) indicates a voltage change. Of course other force sensing elements may be used instead of piezoresistive elements (612), such as conductive elastomers and/or gels, strain gauges, capacitive sensing elements, other resistive sensing elements, and/or etc. It should also be understood that a flexible ring may be positioned about an annular array of piezoresistive elements (612) or substitutions thereof. Such a flexible ring may at least partially support the piezoresistive elements (612) or substitutions thereof in an annular array; may elastically deform in response to pressure exerted by a surgeon's hand, thereby transmitting forces to the piezoresistive elements (612) or substitutions thereof; and/or may act as a seal preventing the piezoresistive elements (612) or substitutions thereof from being exposed to fluids, etc. In some other versions, as will be described in greater detail below, a Hall Effect sensor may be used for a non-contact based determination of the force using the proximity of a finger (656) relative to the Hall Effect sensor. Of course still other configurations for piezoresistive elements (612) will be apparent to one of ordinary skill in the art in view of the teachings herein.

End effector (650) of the present example includes a waveguide (660) rotatably disposed within a casing (652). Waveguide (660) comprises a member configured to couple to distal resonator (634) to transmit the ultrasonic vibrations from transducer (620) to a blade (not shown) or other feature coupled to a distal end of waveguide (660). As shown in FIG. 9, waveguide (660) includes a proximal threaded recess (662) (shown in phantom) configured to couple to threaded portion (640) to mechanically and harmonically couple waveguide (660) to transducer (620). Of course other coupling features for waveguide (660) and/or transducer (620) will be apparent to one of ordinary skill in the art in view of the teachings herein. Casing (652) includes a bushing (654) to support waveguide (660) while still permitting waveguide (660) to rotate and vibrate relative to casing (652). Of course it should be understood that other rotatable couplings may be provided, such as bearings, or, in some versions, bushing (654) may be omitted.

Casing (652) includes a pair of fingers (656) at a proximal end of casing (652). As discussed above, fingers (656) are configured to contact piezoresistive elements (612) when force is applied to a blade or other feature of end effector (650). In the present example, fingers (656) comprise two crescent-shaped cantilever members that are 180 degrees apart from each other, as shown best in FIG. 10. Referring to FIG. 10, when a force is applied horizontally, at least one finger (656) engages one or more piezoresistive elements (612). Accordingly, the voltage output from the corresponding piezoresistive elements (612) may be used to determine both the direction of the force (via which piezoresistive element(s) (612) changed voltage) and the magnitude (via the change in voltage). If a force is applied vertically relative to the example shown in FIG. 10, the crescent-shape of fingers (656) contacts at least one or more piezoresistive elements (612) above or below fingers (656). Accordingly, with two fingers (656), the direction and magnitude of force can be resolved for any direction of force on the blade or other feature of end effector (650). Of course more than two fingers (656) may be used. For instance, three fingers (656) may be spaced 120 degrees apart. Such fingers (656) may be of any geometry, including simple rectangular members. Further still, in some versions a single finger (656) may be used with concentric rings of piezoresistive elements (612), having an outer ring of piezoresistive elements (612) and an inner ring of piezoresistive elements (612). Accordingly, the single finger (656) will always contact either a piezoresistive elements (612) on the interior ring or the exterior ring in response to a force on the blade or other feature of the end effector (650). In some further versions, fingers (656) may not necessarily be associated with casing (652) of end effector (650), but may instead be associated with a separate feature of end effector (650). In addition, or in the alternative, piezoresistive elements (612) may be associated with end effector (650) while fingers (656) extend from casing (602) of handle assembly (600). Still further configurations for end effector (650) and/or fingers (656) will be apparent to one of ordinary skill in the art in view of the teachings herein.

E. Piezoelectric Strip Directional Force Sensor Assembly

Figure 11A:
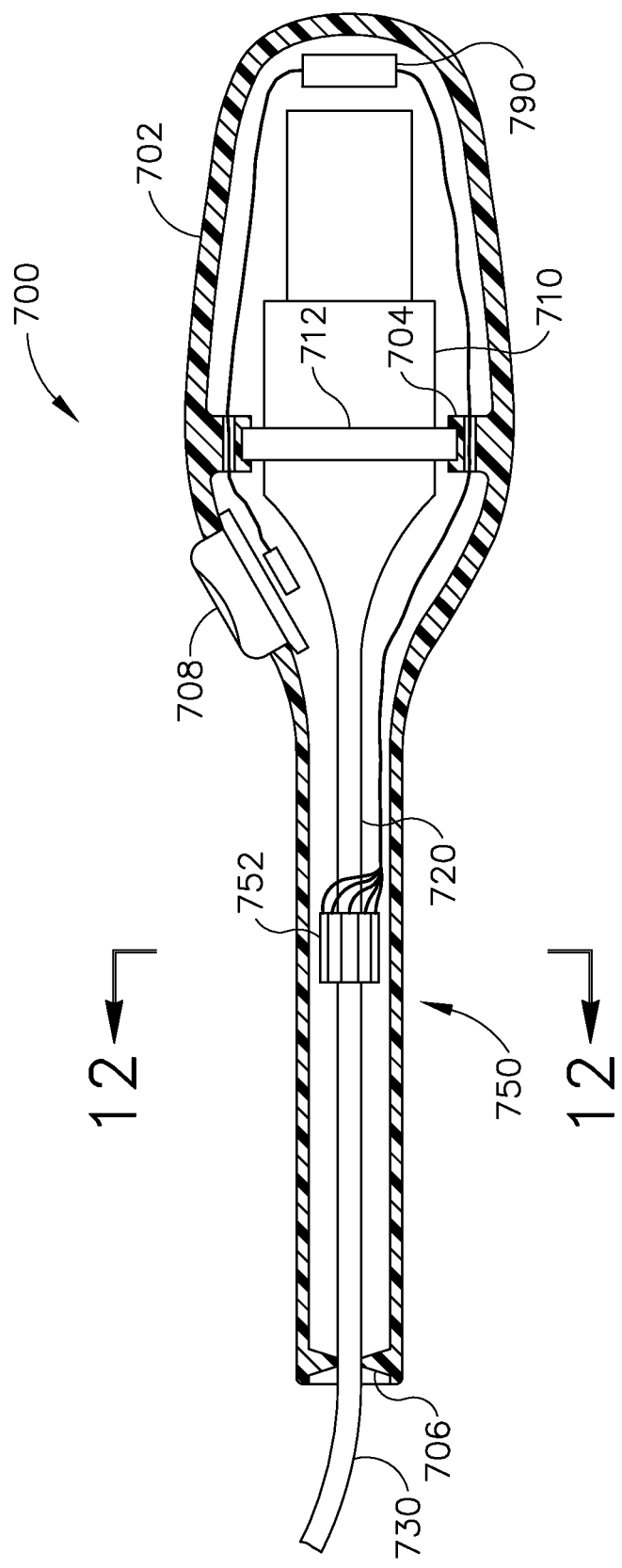
FIG. 11A depicts a side elevation view of an exemplary surgical instrument having a portion of a casing removed to show an exemplary alternative directional force sensor assembly shown in a first, unflexed state.

FIGS. 11A-13B depict an exemplary alternative surgical instrument (700) comprising a casing (702), a transducer (710) rotatably mounted within casing (702), a waveguide (720) extending from transducer (710), a blade (730) coupled to a distal end of the waveguide (720), and a directional force sensor assembly (750). Referring initially to FIGS. 11A-11B, casing (702) of the present example is sized and configured to contain transducer (710), a controller (790), and other components (not shown) therein. Casing (702) may be constructed from a durable plastic (such as polycarbonate or a liquid crystal polymer), ceramics and/or metals or any other suitable material as will be apparent to one of ordinary skill in the art in view of the teachings herein. In the present example, a power source and the associated wiring to power transducer (710) and to be controlled by controller (790) has been omitted for clarity. In some versions casing (702) may include a proximally extending cable (not shown) that carries a plurality of wires (not shown) to a power source, such as generator (40) described above. Of course, in some versions the cable may be omitted and the power source may be located within casing (702).

Casing (702) in the present example further comprises a transducer mount (704) and a front node (706). Transducer mount (704) is configured to longitudinally secure transducer (710) within casing (702) while permitting transducer (710) to rotate therein. By way of example only, transducer mount (704) comprises a bearing feature that interfaces with a flange (712) on transducer (710). Front node (706) comprises a pair of fulcrums that interface with and support waveguide (720) at a distal end of casing (702). Accordingly, the ultrasonic assembly of transducer (710), waveguide (720), and blade (730) are supported at two fixed points of instrument (700).

Casing (702) also includes an activation button (708). Activation button (708) is electrically coupled to controller (790) and is operable to instruct controller (790) to selectively activate instrument (700) in response to a user using activation button (708). Activation button (708) may include a trigger, a capacitive touch sensor, a resistive touch sensor, an electromechanical button, and/or any other activation button (708) as will be apparent to one of ordinary skill in the art in view of the teachings herein. Activation button (708) may be further constructed in accordance with at least some of the teachings of activation feature (18) described herein.

Transducer (710) of the present example comprises an alternating stack of piezoelectric elements and electrodes that are operable to vibrate waveguide (720) when power is applied to the electrodes. Waveguide (720) extends distally from transducer (710) and is mechanically coupled to transducer (710) at a proximal end. Blade (730) is coupled to a distal end of waveguide and is operable to cut and/or coagulate when transducer (710) is active. In some versions, blade (730) is keyed to waveguide (720) such that the rotational position of blade (730) relative to waveguide (720) is known. Such rotational position information may be used by controller (790) during the control of the operation of transducer (710), as will be described herein. Transducer (710), waveguide (720), and/or blade (730) may be further constructed in accordance with at least some of the teachings of transducers (90, 210, 320, 620), waveguides (160, 360, 660), blades (82, 152) and/or otherwise.

As noted above, controller (790) is contained within casing (702). Controller (790) is operable to control the energy settings of a power source to control the output from transducer (710) that is transmitted to blade (730) via waveguide (720). Controller (790) is electrically coupled to directional force sensor assembly (750), as will be described in greater detail below, and to activation button (708). In some versions, controller (790) may be configured such that, even if activation button (708) is operated by a user, transducer (710) does not activate until a force is detected by directional force sensor assembly (750), though this is merely optional. Controller (790) may be further constructed in accordance with at least some of the teachings of control module (12) described above.

Figure 11B:
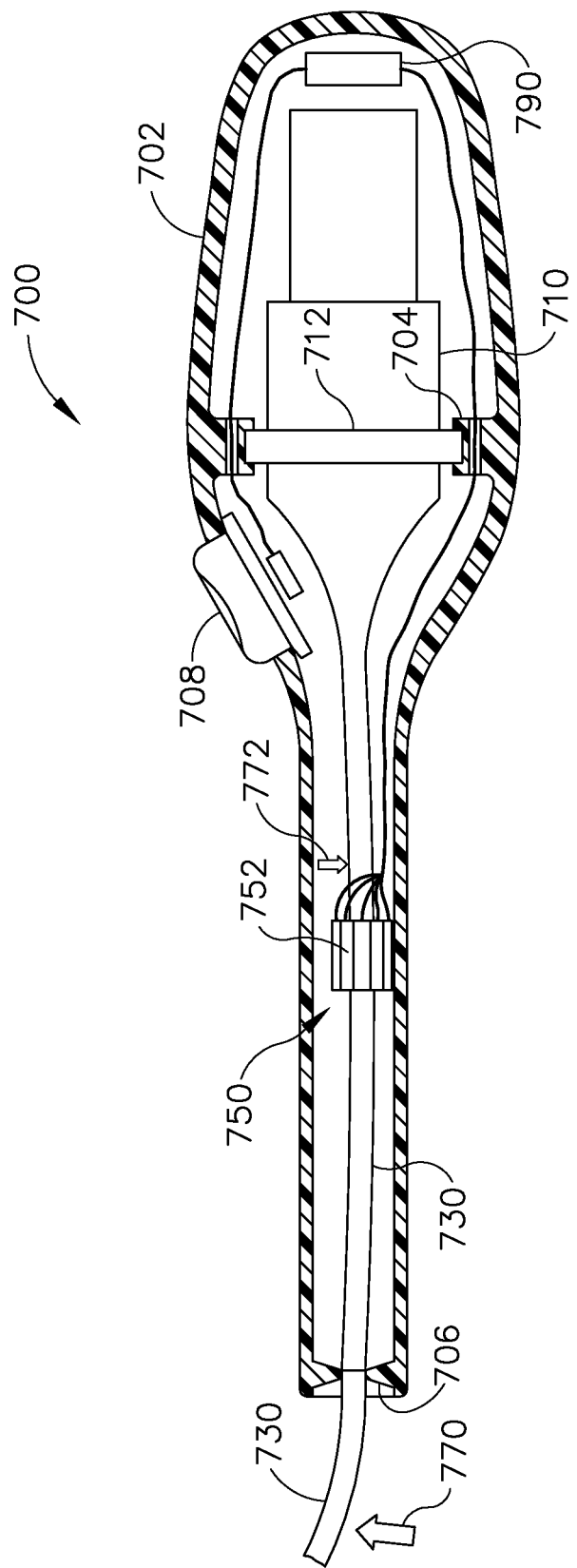
FIG. 11B depicts the surgical instrument and directional force sensor assembly of FIG. 11A shown in a second, flexed state.
Figure 12:
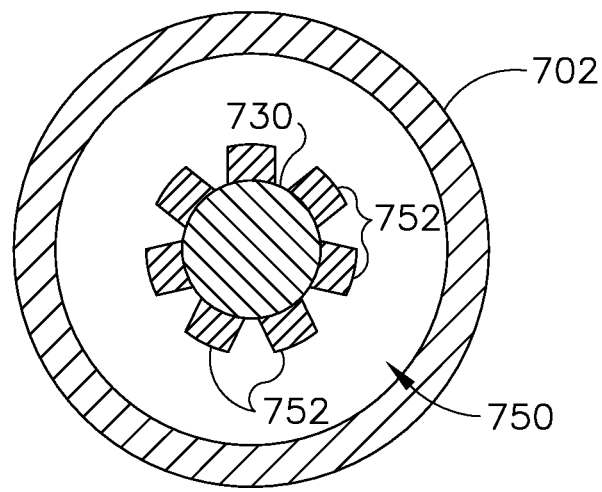
FIG. 12 depicts a cross-sectional view of the directional force sensor assembly of FIGS. 11A-11B taken along section line 12-12 shown in FIG. 11A and showing a plurality of force sensing elements disposed about a waveguide.

Directional force sensor assembly (750) of the present example comprises a plurality of piezoresistive strips (752) disposed about a portion of waveguide (720). In the present example, directional force sensor assembly (750) is located at a midpoint between front node (706) and transducer mount (704) such that the deflection of waveguide (720) relative to a longitudinal axis (780) will be a maximum, though this is merely optional. In addition, directional force sensor assembly (750) is also located at or near a node, or a point where the oscillatory vibrations in waveguide (720) are at a minimum, to minimize the acoustic energy absorbed by sensor assembly (750). In some versions, sensor assembly (750) is located adjacent to a node or asymmetrically straddles a node. Alternatively, sensor assembly (750) may be located at other suitable any point along waveguide (720) as will be apparent to one of ordinary skill in the art in view of the teachings herein. Referring briefly to FIG. 12, piezoresistive strips (752) are disposed in an angular array about waveguide (720) and are fixedly coupled to waveguide (720). In the present example, seven piezoresistive strips (752) are disposed equidistantly around waveguide (720), though this is merely optional. In some versions more than seven or less than seven piezoresistive strips (752) may be used. By way of example only, piezoresistive strips (752) may be adhesively bonded and/or mechanically coupled to waveguide (720). Piezoresistive strips (752) comprise longitudinally elongate members such that flexing of waveguide (720), such as that shown in FIGS. 11A-11B and 13A-13B, extend or compress piezoresistive strips (752). Accordingly, such extension and/or compression generates a voltage that may be measured by a voltage detection device. In the present example, each piezoresistive strip (752) is electrically coupled to controller (790) such that the voltage(s) generated by the flexure of waveguide (720) is transmitted to controller (790).

Controller (790) comprises one or more voltage detection circuits to determine the changes in voltage from each piezoresistive strip (752). Accordingly, controller (790) may be configured to use location of the piezoresistive strip (752) and the voltage generated to determine the direction and magnitude of force applied to blade (730). In some versions, the keying of blade (730) to waveguide (720) may be used as a reference point for determining the direction of the force based upon the location of the voltage-producing piezoresistive strip (752) relative to the predetermined keyed portion. Of course it should be understood that other force sensing elements may be disposed about waveguide (720) as well. For example, a plurality of strain gauges may be longitudinally mounted to waveguide (720). Still other configurations for piezoresistive strips (752) and/or directional force sensor assembly (750) will be apparent to one of ordinary skill in the art in view of the teachings herein.

Figure 13A:
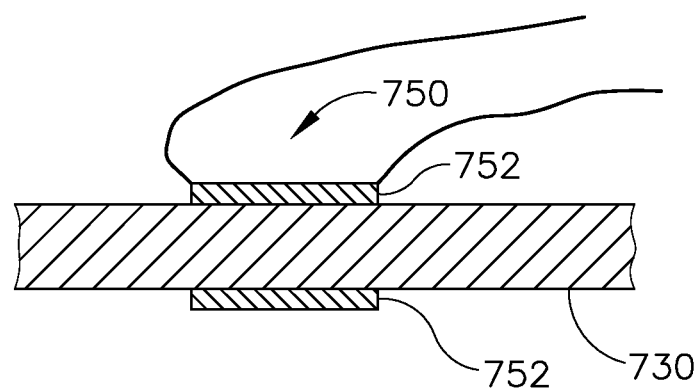
FIG. 13A depicts a partial enlarged cross-sectional view of the directional force sensor assembly of FIG. 11A shown in the first, unflexed state.
Figure 13B:
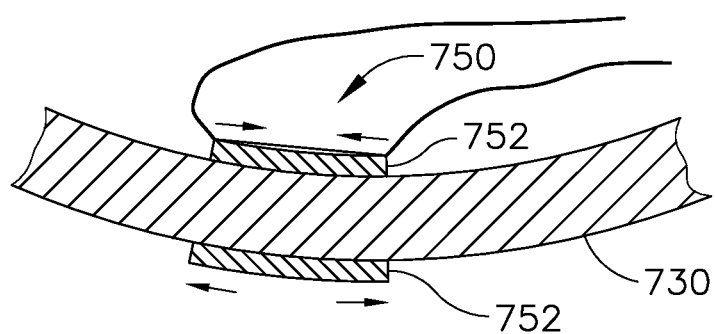
FIG. 13B depicts a partial enlarged cross-sectional view of the directional force sensor assembly of FIG. 11B shown in the second, flexed state.

Referring back to FIG. 11A, blade (730) and waveguide (720) are shown in a first, unflexed state. In this position, piezoresistive strips (752) are be calibrated to output no voltage. In some versions, when transducer (710) is active, the vibrations through waveguide (720) may produce small consistent voltage changes for piezoresistive strips (752) for which controller (790) may be calibrated to ignore. When a force is applied to blade (730), such as that shown in FIG. 11B by arrow (770), front node (706) and transducer mount (704) provide two points between which waveguide (720) flexes in a direction opposing the force applied to blade (730) as indicated by arrow (772). A merely exemplary exaggerated version of such a flexure is shown in FIGS. 13A-13B. When waveguide (720) is in the second, flexed state, one or more piezoresistive strips (752) are compressed while one or more piezoresistive strips (752) are extended. Accordingly, controller (790) detects an increase in voltage from some piezoresistive strips (752) and a decrease in voltage by other piezoresistive strips (752). By identifying which piezoresistive strips (752) have been compressed the most and which piezoresistive strips (752) have been extended the most (e.g., via the change in voltages), controller (790) can determine from what direction about blade (730) the force was applied. In addition, through prior calibration, the voltage change may be used to determine the magnitude of force applied to blade (730). Accordingly, utilizing directional force sensor assembly (750), controller (790) is able to determine the direction and magnitude of force applied to blade (730). Controller (790) may then be configured to apply one or more energy settings to control the output of transducer (710), as will be described in greater detail herein.

F. Non-Contact Directional Force Sensor Assembly

In some versions, it may be preferable to determine the direction and force applied to blade (82, 152, 730) without contacting waveguide (160, 360, 660, 720). One merely exemplary non-contact directional force sensor assembly will now be described; however, it should be understood that other examples will be apparent to those of ordinary skill in the art in view of the teachings herein.

Figure 14:
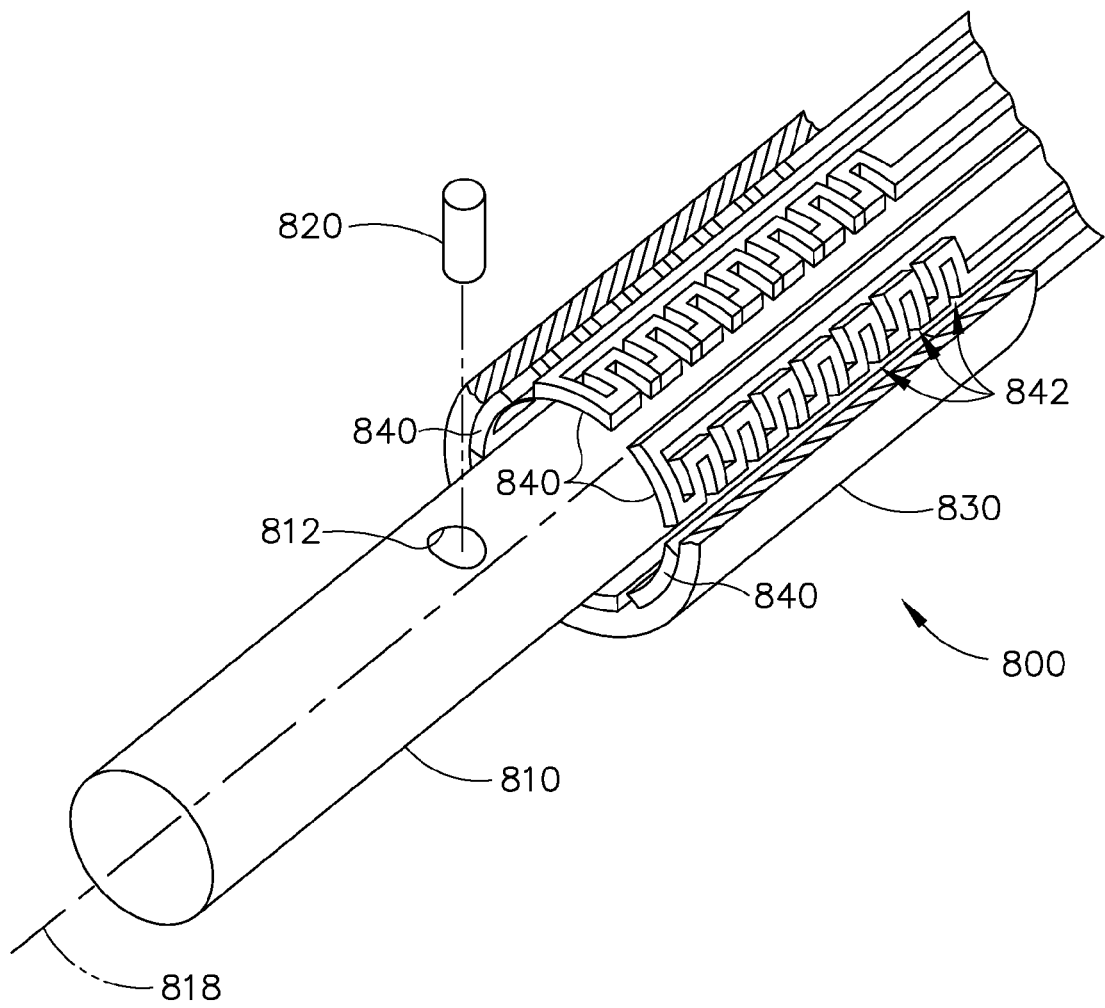
FIG. 14 depicts a partial perspective view of yet another exemplary alternative directional force sensor having a magnet disposed within a portion of a waveguide.
Figure 15:
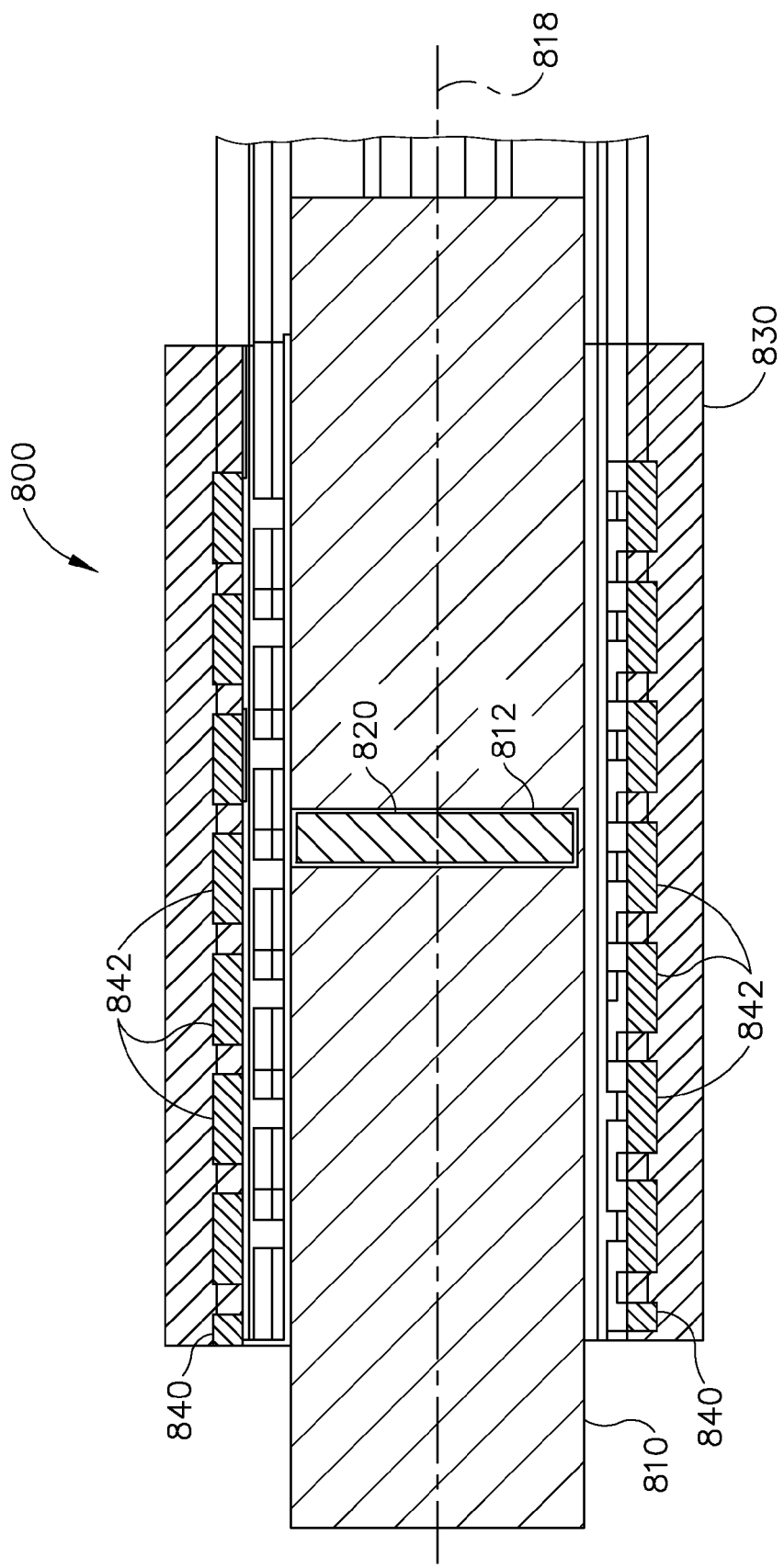
FIG. 15 depicts a partial enlarged cross-sectional view of the directional force sensor showing the magnet disposed within a portion of the waveguide and surrounded by a plurality of looped electrodes.

FIGS. 14-15 show an exemplary non-contact directional force sensor assembly (800) comprising a waveguide (810) disposed within a sheath (830). In the present example, waveguide (810) comprises an elongate metallic member coupled to a transducer (not shown) at a proximal end and to a blade (not shown) at a distal end. Waveguide (810) of the present example includes a transverse hole (812) configured to receive a pin-shaped magnet (820) therein. In the present example, transverse hole (812) comprises a cylindrical hole, though other shapes and geometries will be apparent to one of ordinary skill in the art in view of the teachings herein. Magnet (820) and hole (812) are configured such that magnet (820) is substantially centered about a longitudinal axis (818) of waveguide (810) when magnet (820) is inserted into hole (812). In some versions, an adhesive or other feature may secure magnet (820) within hole (812), though this is merely optional. In addition, or in the alternative, magnet (820) may be overmolded with silicone to insulate magnet (820) relative to waveguide (810), though this is merely optional. In the present example, magnet (820) is magnetized along the axis of the pin shape that is formed by magnet (820). Moreover, while the foregoing has been described in reference to waveguide (810), it should be understood that magnet (820) and hole (812) may be located on a blade and/or on a portion of a transducer as will be apparent to one of ordinary skill in the art in view of the teachings herein.

Sheath (830) includes a plurality of electrode loops (840) disposed in an angular array on sheath (830). Sheath (830) of the present example comprises a plastic member having electrode loops (840) overmolded onto an interior surface of sheath (830), though this is merely optional. In some versions electrode loops (840) may be overmolded onto the exterior of sheath (830) and/or associated with sheath (830) through other means (e.g., adhesive attachment, mechanical couplings, etc.). Electrode loops (840) each comprise a metallic wire or component having a plurality of short lateral switchbacks (842) along a longitudinal length. In some variations, electrode loops (840) are formed as continuous windings around the diameter of sheath (830). Such loops may be centered over the location of magnet (820), such that the axis of the pin shape that is formed by magnet (820) passes through the center of electrode loops (840). In addition or in the alternative, electrode loops (840) may be wound around the circumference of sheath (830). Other suitable configurations for electrode loops (840) and/or sheath (830) will be apparent to one of ordinary skill in the art in view of the teachings herein.

Referring to FIG. 15, when waveguide (810) is oscillating due to a transducer driving the oscillations, magnet (820) is moved longitudinally back and forth along axis (818) relative to sheath (830). This oscillatory motion results in the generation of a small current in electrode loops (840) that may be measured by a controller and/or control module, such as controller (790) and/or control module (12). When waveguide (810) is deflected, such as by a user pressing a blade against tissue or, magnet (820) is moved closer to one or more electrode loops (840). The increased magnetic field results in an increased induced current in the corresponding electrode loops (840). Accordingly, the orientation of the deflection can be determined via which electrode loop(s) (840) experience and increase and/or decrease in current, and the magnitude of the force causing the deflection can be determined based upon the structural characteristics of waveguide (810) and the magnitude of current increase. Thus, both the magnitude and direction of force applied to a blade coupled to waveguide (810) can be determined without contacting waveguide (810). Sheath (830) may be operated in a resonant circuit that would be sensitive to small changes in the effective inductance of the relative mechanical motion of the magnet (820) and sheath (830) assembly. The resonance of the circuit would vary with the effective inductance. Of course still other arrangements and/or configurations for non-contact directional force sensor assembly (800) will be apparent to one of ordinary skill in the art in view of the teachings herein.

IV. Exemplary Damping Control

As noted above, in some instances it may be preferable to damp the ultrasonic drive train of an instrument (10, 50, 100, 700) or otherwise control the oscillatory motion. For instance, if a transverse motion occurs in a waveguide (160, 360, 660, 720, 810) and/or other portion of the ultrasonic drive train of surgical instrument (10, 50, 100, 700) due to the blade bearing against tissue during a surgical procedure, the transverse motion may disrupt or otherwise interfere with the oscillatory motion from transducer (90, 210, 320, 620, 710). In addition, in some cases the transverse motion may induce an unstable mode of vibration, thereby potentially damaging instrument (10, 50, 100, 700). Elimination or reduction of these transverse motions during the use of surgical instrument (10, 50, 100, 700) may permit larger manufacturing tolerances. Accordingly, various methods of damping such transverse motions out of the ultrasonic drive train will now be described, though other examples will be apparent to one of ordinary skill in the art in view of the teachings herein.

Figure 16:
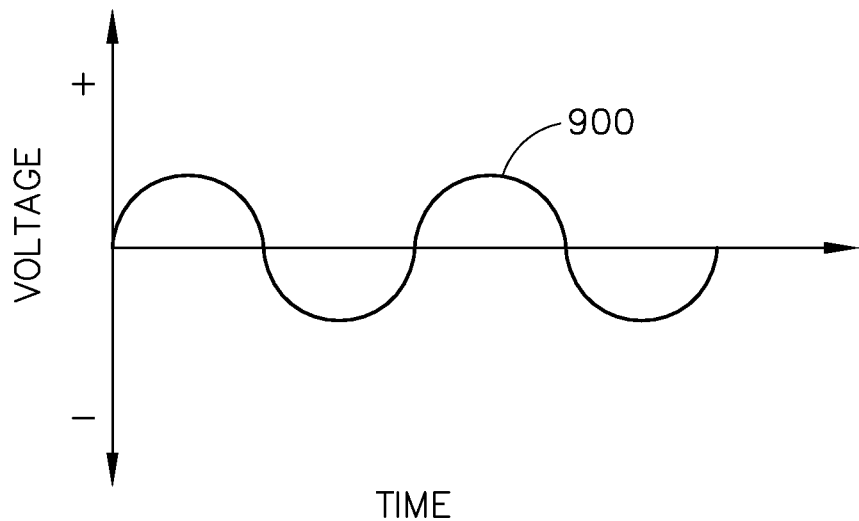
FIG. 16 depicts a graphical view of the voltage over time detected by a voltage sensing device showing a normal output when a transducer is vibrating at a natural frequency.
Figure 17:
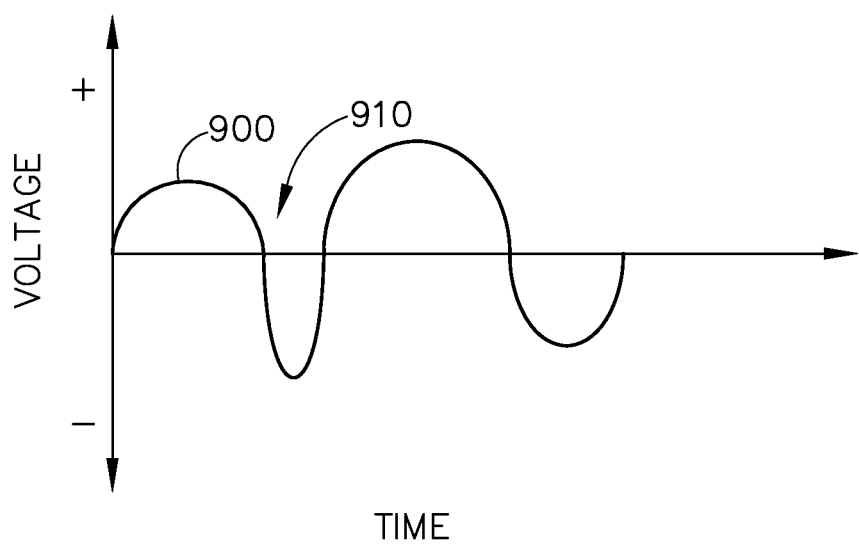
FIG. 17 depicts a graphical view of the voltage over time detected by a voltage sensing device showing a transverse event.

FIG. 16 depicts an exemplary sample voltage output (900) from distal piezoelectric disc assembly (250) of FIG. 5 when transducer (210) is operating in a normal state. When a transverse motion or event is applied to an end effector and/or waveguide, a disturbance (910) in the oscillatory waveform occurs and causes voltage output (900) to become unstable, as shown in FIG. 17. Of course it should be understood that the foregoing are merely exemplary.

Figure 18:
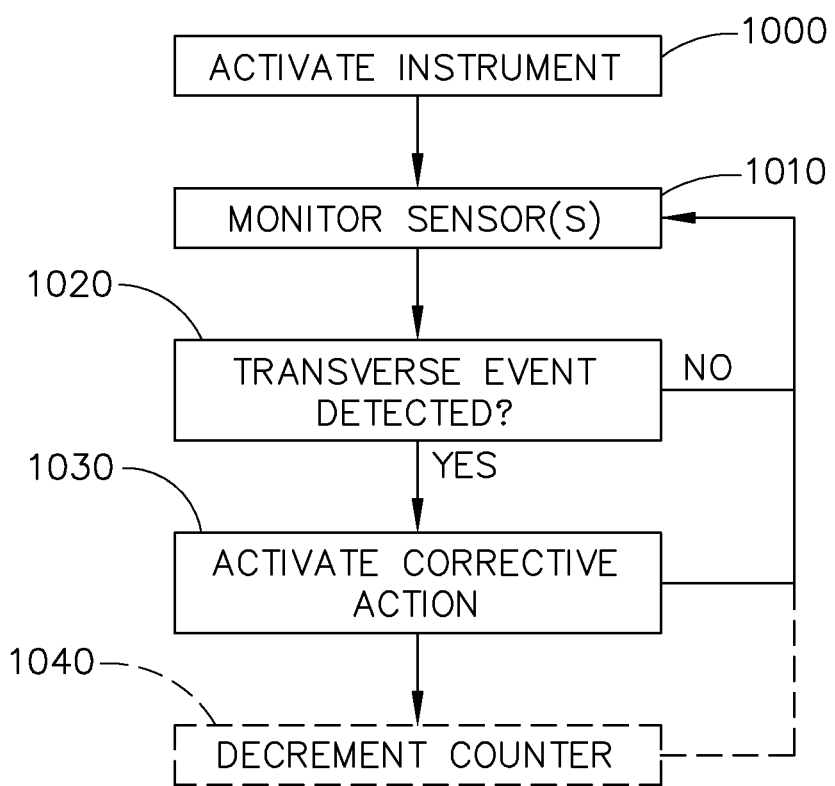
FIG. 18 depicts a flowchart of exemplary steps to correct for a transverse event experienced by an ultrasonic drive train.

FIG. 18 depicts an exemplary flowchart of steps that may be performed by a control module, such as control module (12) and/or controller (790), for correcting the motion of the ultrasonic drive train in response to a transverse event, such as that shown in FIG. 17. At step (1000), an instrument, such as instruments (10, 50, 100, 700) is activated. At step (1010), one or more sensors of the instrument are monitored. By way of example only, distal piezoelectric disc assemblies (250), piezoelectric disc assembly (370), multi-piece piezoelectric element (400), and/or multi-piece piezoelectric element (500) may be monitored by the control module. In the present example, the monitoring performed at step (1010) comprises monitoring the voltage output (900) from one or more of the foregoing sensors. At step (1020), the control module determines whether a transverse event has been detected. Such a determination may be made by detecting whether the voltage output (900) has exceeded a predetermined threshold and/or whether the period of the oscillatory waveform has changed, such as that shown in FIG. 17. If no transverse event is detected, the control module returns to step (1010) to continue monitoring the sensors.

Figure 19:
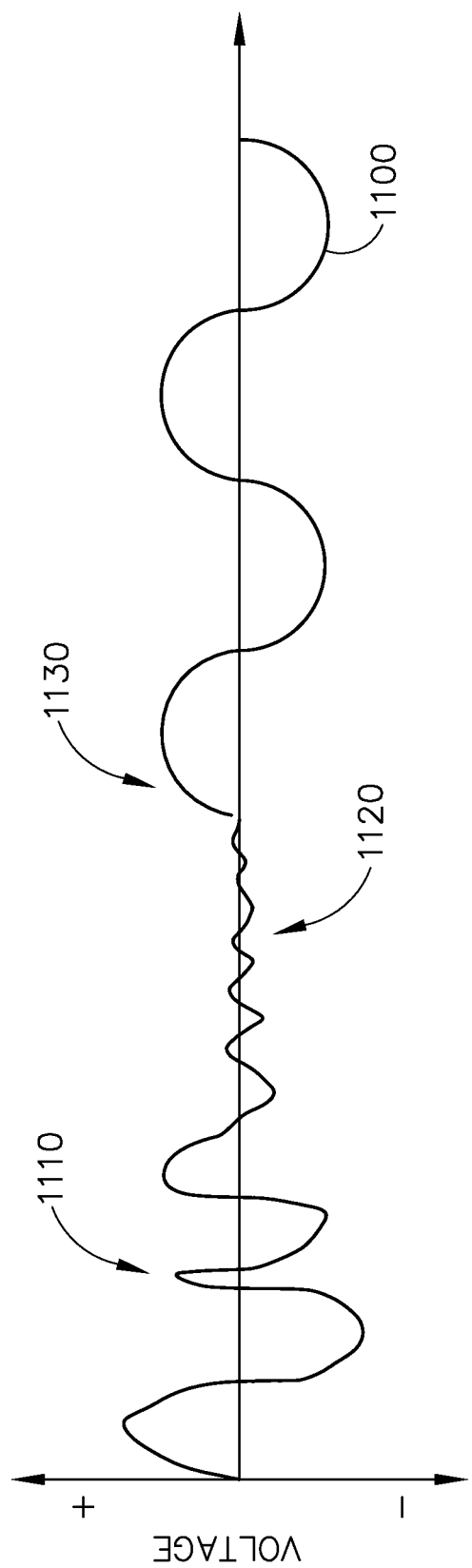
FIG. 19 depicts a graphical view of the voltage over time detected by a voltage sensing device showing an exemplary first corrective action to dampen a transverse event.

If a transverse event is detected, the control module proceeds to step (1030) where a corrective action is activated. One exemplary corrective action is shown in FIG. 19, where the control module temporarily deactivates the transducer to let the oscillation ebb and then reactivates the transducer to resume operation of the instrument. As shown in FIG. 19, the voltage output (1100) is initially unstable due to a transverse event. At region (1110), the transducer is deactivated. The vibrations ebb through region (1120). At region (1130), the transducer is reactivated to resume normal operation.

Figure 20:
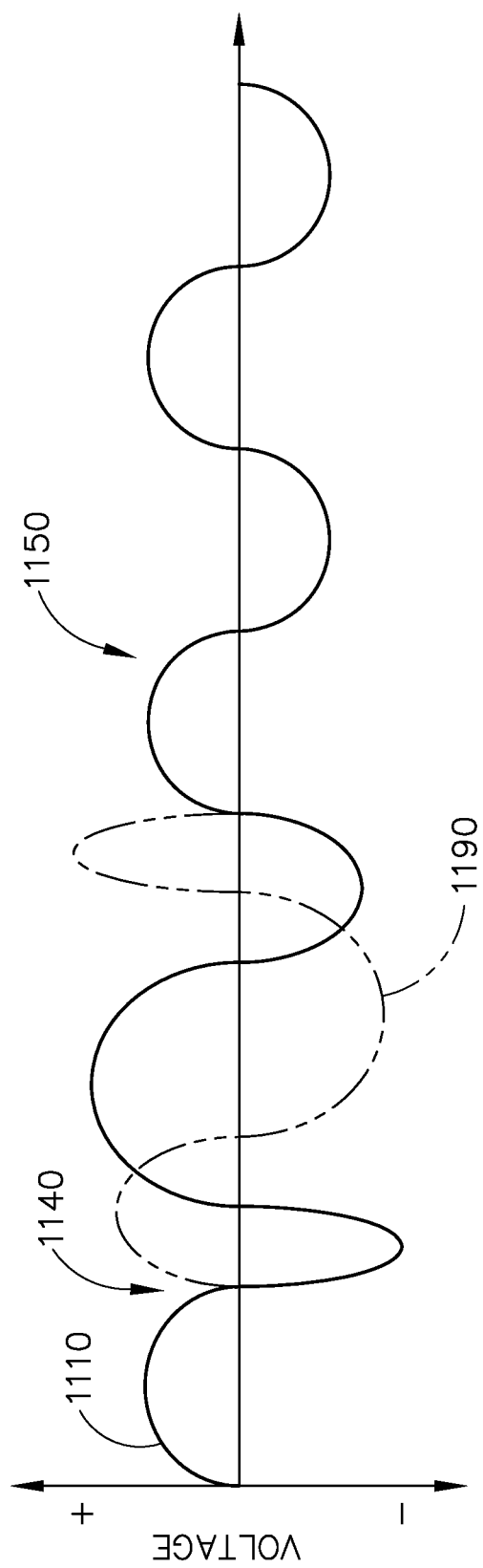
FIG. 20 depicts a graphical view of the voltage over time detected by a voltage sensing device showing an exemplary second corrective action to dampen a transverse event.

A second exemplary corrective action that may be implemented at step (1030) is shown in FIG. 20, where an active damping of the instability is performed. By way of example only, such active damping may be done by distal piezoelectric disc assemblies (250), piezoelectric disc assembly (370), multi-piece piezoelectric element (400), and/or multi-piece piezoelectric element (500) as described above. In the example shown in FIG. 20, the solid voltage output (1100) corresponds to the vibrations sensed by one or more of distal piezoelectric disc assemblies (250), piezoelectric disc assembly (370), multi-piece piezoelectric element (400), and/or multi-piece piezoelectric element (500) as described above, and/or by one or more segments (410, 420, 430, 440, 530). The dashed voltage input (1190) corresponds to the voltage provided to one or more of distal piezoelectric disc assemblies (250), piezoelectric disc assembly (370), multi-piece piezoelectric element (400), multi-piece piezoelectric element (500), and/or by one or more segments (410, 420, 430, 440, 530) to actively damp a transverse event.

As shown in FIG. 20, voltage output (1100) initially indicates a transverse event at (1140). The control module then activates one or more of distal piezoelectric disc assemblies (250), piezoelectric disc assembly (370), multi-piece piezoelectric element (400), multi-piece piezoelectric element (500), and/or by one or more segments (410, 420, 430, 440, 530) in accordance with voltage input (1190) to actively damp the instability of indicated by voltage output (1100). By way of example only, the active damping to produce voltage input (1190) may comprise activating the distal piezoelectric disc assemblies (250), piezoelectric disc assembly (370), multi-piece piezoelectric element (400), multi-piece piezoelectric element (500), and/or by one or more segments (410, 420, 430, 440, 530) at the peak of the oscillatory waveform of voltage output (1100) to counter the transverse event. In some versions, the activation of active damping features may be done for short bursts followed by detecting the oscillatory waveform of voltage output (1100). The new voltage output (1100) reading may be used to modify the active damping being performed and/or to determine whether the system has returned to a normal oscillatory waveform. For instance, at (1150) the instability from the transverse event indicated by voltage output (1100) has been subdued. Alternatively, the activation of the active damping features may be done continuously once the transverse event was detected and be deactivated after a predetermined time and/or once another sensor determines the unstable waveform has ceased. In addition, in some versions the control module may include a predetermined limitation for the maximum voltage input (1190) that may be applied during the active damping, though this is merely optional. Of course other configurations for active damping will be apparent to one of ordinary skill in the art in view of the teachings herein.

Returning to FIG. 18, once the corrective actions described above have suppressed and/or substantially suppressed the transverse event, the control module may return to monitoring the sensors at step (1010). In some versions, optional step (1040) decrements a counter after each corrective action is preformed at step (1030). By way of example only, an instrument may be limited to correction of 100 transverse events. Once the counter reaches zero, an indicator may be activated to notify the user that the instrument is operating outside of the acceptable parameters (e.g., informing the user by activating a light, a beep, a vibration, etc.). In addition, or in the alternative to the notification, the control module may deactivate the transducer until the instrument is repaired or reclaimed. If the counter has not decreased to zero at step (1040), then the control module returns to step (1010) to monitor the sensors again. Of course other configurations and steps will be apparent to one of ordinary skill in the art in view of the teachings herein.

V. Exemplary Energy Setting Management

In some versions it may be useful to adjust the energy settings of an instrument (10, 50, 100, 700) based upon how the user is utilizing the instrument (10, 50, 100, 700). For instance, for some users, the direction and magnitude of force applied to the blade (82, 152, 730) may be indicative of the type of use and energy settings expected by the user. For instance, if the user applies light pressure using a side face of blade (82, 152, 730), such as in the direction of arrows (192, 194) shown in FIG. 4, then the user may be expecting to use the blade to coagulate tissue. Alternatively, if the user applies more forceful pressure using a top or bottom face of blade (82, 152, 730), such as in the direction of arrows (196, 198) shown in FIG. 4, then the user may be expecting to use the blade to cut tissue. Accordingly, using one or more of the foregoing multi-piece piezoelectric elements (400, 500), piezoresistive elements (612) and fingers (656), and/or directional force sensor assemblies (750, 800) to detect both the magnitude and direction of the force applied to blade (82, 152, 730), a control module, such as control module (12) and/or controller (790), may be used to control the energy settings for a transducer (90, 210, 320, 620, 710). Some merely exemplary energy setting control configurations will now be described; however, it should be understood that other configurations to control the energy settings of the transducer (90, 210, 320, 620, 710) will be apparent to one of ordinary skill in the art in view of the teachings herein.

Figure 21:
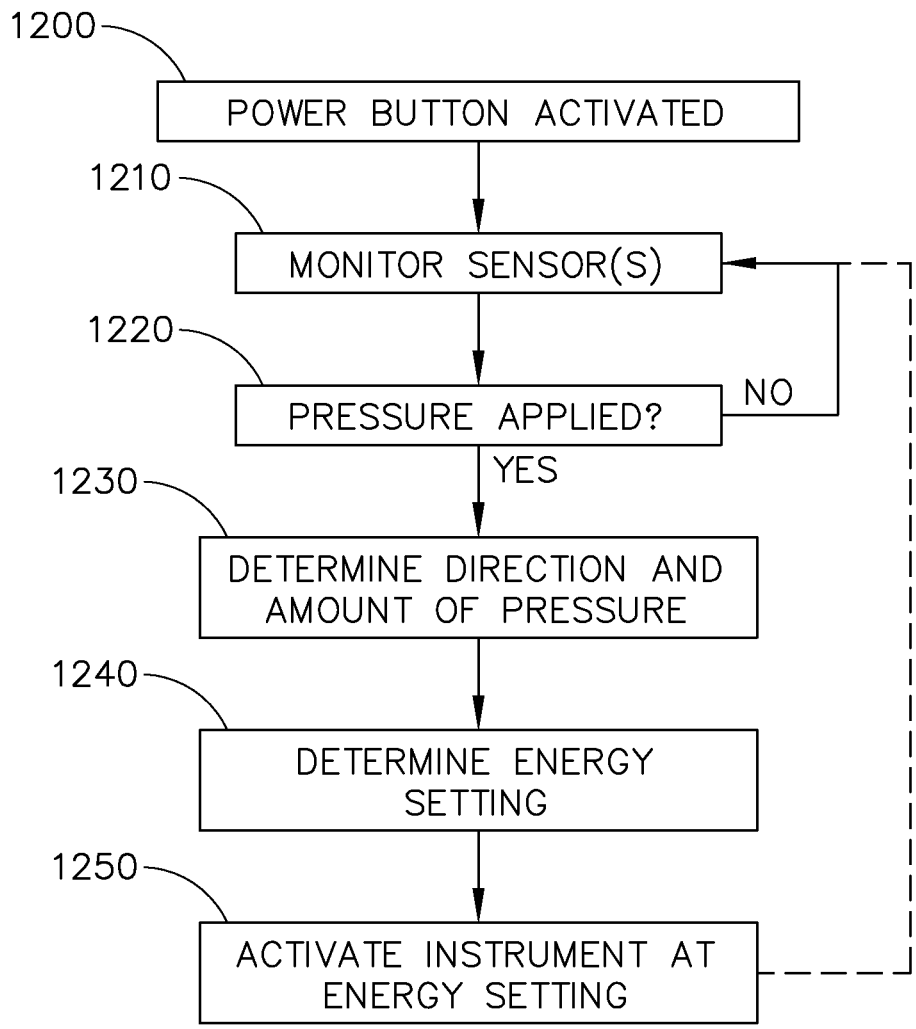
FIG. 21 depicts a flowchart of exemplary steps for controlling the energy settings of a surgical instrument based upon a direction and magnitude of force applied to an end effector.

FIG. 21 depicts one merely exemplary flowchart of exemplary steps for controlling the energy settings for a transducer (90, 210, 320, 620, 710). The present example will be described in reference to instrument (700) shown and described in reference to FIGS. 11A-13B, though it should be understood that the following is applicable to any other surgical instruments (10, 50, 100, 700) described herein, surgical instruments incorporating one or more of multi-piece piezoelectric elements (400, 500), piezoresistive elements (612) and fingers (656), and/or directional force sensor assemblies (750, 800), and/or any other surgical instrument, as will be apparent to one of ordinary skill in the art in view of the teachings herein.

At step (1200), a single activation or power button (708) is initially activated by the user. As noted above, activation button (708) may include a trigger, a capacitive touch sensor, a resistive touch sensor, an electromechanical button, and/or any other activation button (708) as will be apparent to one of ordinary skill in the art in view of the teachings herein. The use of a single activation button (708) may simplify instrument (700) such that a user need not switch between various energy level setting buttons, such as a max or min energy toggle, during use of the instrument (700), though this is merely optional. In the present example, operation of activation button (708), alone, does not activate transducer (710), though in some versions, operating the activation button (708) may initiate transducer (710). At step (1210), controller (790) monitors directional force sensor assembly (750). At step (1220), controller (790) determines whether force has been detected by directional force sensor assembly (750). For example, if waveguide (720) deflects, such as that shown in FIGS. 11B and 13B, piezoresistive strips (752) deform and produce a change in voltage. Controller (790) detects this change in voltage and determines that a force is being applied to blade (730) and proceeds to step (1230). If no force is detected on blade (730), controller (790) continues to monitor directional force sensor assembly (750) at step (1210) until a force is detected by directional force sensor assembly (750). In the present example, transducer (710) is activated only after both activation button (708) is operated by the user and controller (790) detects that a force is applied to blade (730) via directional force sensor assembly (750) while activation button (708) is depressed. Such a configuration may provide a lock-out feature to reduce inadvertent activation. Of course the foregoing is merely optional.

At step (1230), controller (790) utilizes the configuration of directional force sensor assembly (750) to determine both the magnitude and direction of the force applied to blade (730). As described above, piezoresistive strips (752) are disposed about waveguide (720) in an angular array such that the direction of force applied to blade (730) can be detected. By way of example only, as shown in FIG. 11B, if a force is applied to the bottom of blade (730), a corresponding piezoresistive strip (752) on the bottom of waveguide (720) would be extended and/or a piezoresistive strip (752) on the top of waveguide (720) would be compressed, thereby producing a dissimilar voltage change that indicates that a force is applied to the bottom of blade (730). Of course it should be understood that the two piezoresistive strips (752) may be used to average the magnitude and direction measurements and/or confirm that one piezoresistive strip (752) is not outputting a faulty voltage reading, though this is merely optional. In some versions, a single piezoresistive strip (752) may be used for each direction, though this is also optional. In addition, or in the alternative, in versions where transducer (710) may already be active, the use of two dissimilar voltage changes indicate a bending of waveguide (720), while parallel and consistent voltage changes may indicate normal operation of the active transducer (710), though this is optional as well. With the magnitude and direction of the force applied to blade (730) determined, controller (790) proceeds to determining the energy setting for transducer (710) at step (1240).

Referring briefly to FIG. 4, if directional force sensor assembly (750) indicates a force applied in the direction of arrows (192, 194) controller (790) determines a predetermined first energy setting at step (1240). If directional force sensor assembly (750) indicates a force applied in the direction of arrows (196, 198) controller (790) determines a predetermined second energy setting at step (1240). In some versions, the first and/or second energy settings may be scaled up or down based upon the magnitude of the force applied to blade (730). In addition, or in the alternative, predetermined minimums and/or maximums for the first energy setting and/or the second energy setting may be set such that a bounded range of energy settings are available for first energy setting and/or second energy setting. In some versions, controller (790) may determine that a force is being applied in a direction other than arrows (192, 194, 196, 198) and may apply an intermediate or other calculated energy setting based upon the direction relative to arrows (192, 194, 196, 198) (e.g., an energy setting determined between the first and second energy setting based upon the angle the force is applied to blade (730)). Still other energy settings and/or configurations for determining the energy settings will be apparent to one of ordinary skill in the art in view of the teachings herein.

With the energy setting determined at step (1240), controller (790) activates transducer (710) at step (1250). In some versions, transducer (1250) remains active for a predetermined period of time at the energy setting determined at step (1240). In addition, or in the alternative, transducer (710) deactivates once the directional force sensor assembly (750) ceases to detect a force being applied to blade (730). Still further, controller (790) may continue to monitor the sensors at step (1210) to detect additional changes in the magnitude and direction of force as measured by directional force sensor assembly (750). Accordingly, controller (790) may be configured to continually update and adjust the energy settings for transducer (710) based upon the magnitude and direction of force applied to blade (730). Thus, a user may simply use instrument (700) in accordance with expected directional force profiles to have instrument (700) dynamically adjust during use. Of course still other configurations will be apparent to one of ordinary skill in the art in view of the teachings herein.

Figure 22:
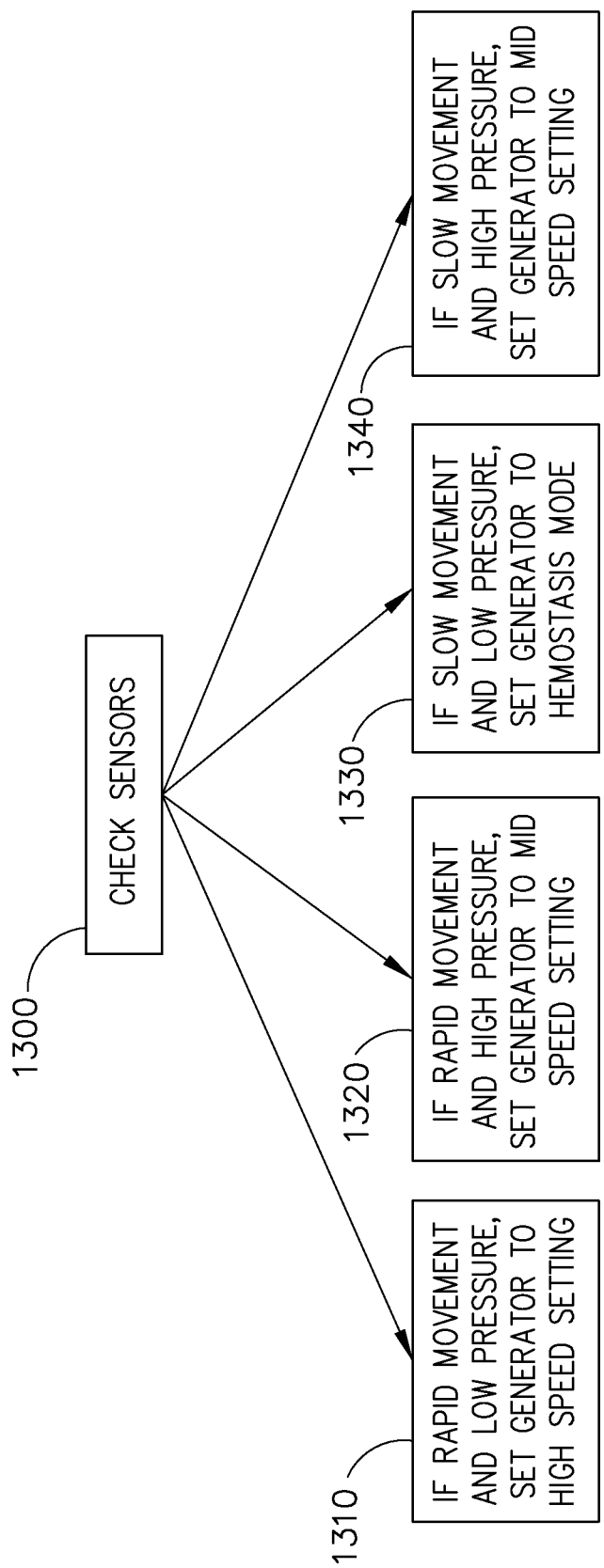
FIG. 22 depicts a flowchart of exemplary steps for controlling the energy settings of a surgical instrument based upon the force applied to an end effector and the speed of movement of the surgical instrument.

For example, as shown in FIG. 22, a merely exemplary alternative configuration to step (1240) for determining the energy settings for transducer (710) is depicted. In the present example, an accelerometer is included in step (1300) when sensors are checked. Based upon magnitude of force detected by directional force sensor assembly (750) and the speed of movement detected by the accelerometer, controller (790) adjusts the energy settings for transducer (710) in accordance with those shown at steps (1310, 1320, 1330, and 1340). At step (1310), if rapid movement is indicated by the accelerometer and a low force or pressure is indicated by directional force sensor assembly (750), then transducer (710) is set to a high speed setting for tissue dissection. If rapid movement is indicated by the accelerometer and a high force or pressure is indicated by directional force sensor assembly (750), then transducer (710) is set to a mid speed setting for cutting through tough tissue or vessels at step (1320). If slow movement is indicated by the accelerometer and a low force or pressure is indicated by directional force sensor assembly (750), then transducer (710) is set to a hemostasis setting for coagulating tissue at step (1330). If slow movement is indicated by the accelerometer and a high force or pressure is indicated by directional force sensor assembly (750), then transducer (710) is set to a mid speed setting for tissue dissection of tough tissue or vessel at step (1340). Controller (790) may continue to check the sensors at (1300) to update the energy setting and/or may proceed in accordance with the steps discussed in reference to FIG. 21. Of course the foregoing is merely exemplary and other configurations will be apparent to one of ordinary skill in the art in view of the teachings herein.

While the foregoing has been discussed in reference to instrument (700), it should be understood that any of the above-described configurations are applicable to any other surgical instruments (10, 50, 100, 700) described herein, to surgical instruments incorporating one or more of multi-piece piezoelectric elements (400, 500), piezoresistive elements (612) and fingers (656), and/or directional force sensor assemblies (750, 800), and/or to any other surgical instrument, as will be apparent to one of ordinary skill in the art in view of the teachings herein.

VI. Exemplary User Feedback Control

In addition, or in the alternative, to the foregoing energy setting management, in some versions it may be preferable to provide feedback to the user to indicate whether their use of an instrument (10, 50, 150, 700) is within a predetermined and/or optimal range for the intended task (e.g., cutting, coagulating, etc.). Such feedback may improve a user's effectiveness with the instrument (10, 50, 150, 700) and/or may reduce the learning curve required to use the instrument (10, 50, 150, 700) within the optimal range(s). As with the above description, while the below example will be described in reference to instrument (700) shown and described in reference to FIGS. 11A-13B, it should be understood that the following is applicable to any other surgical instruments (10, 50, 100, 700) described herein, surgical instruments incorporating one or more of multi-piece piezoelectric elements (400, 500), piezoresistive elements (612) and fingers (656), and/or directional force sensor assemblies (750, 800), and/or any other surgical instrument, as will be apparent to one of ordinary skill in the art in view of the teachings herein.

Figure 23:
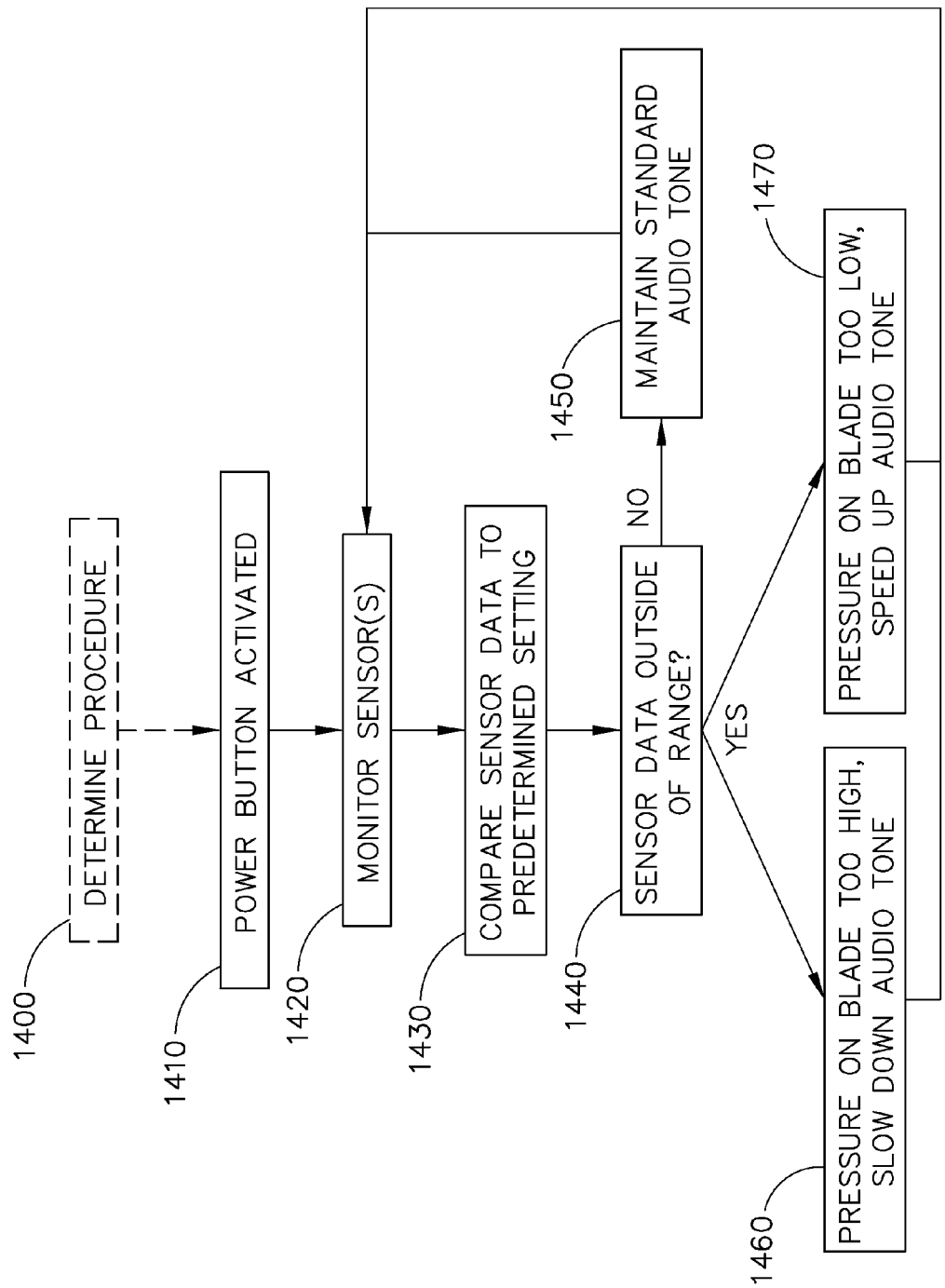
FIG. 23 depicts a flowchart of exemplary steps for providing feedback to a user based upon sensor data.

FIG. 23 depicts an exemplary flowchart depicting a plurality of steps for providing audible feedback to the user based upon their performance with a surgical instrument, such as surgical instrument (700). An initial step (1400) of determining the procedure may be accomplished by loading a procedure configuration data from a storage device, such as module (182) described above and/or module (590) described in U.S. patent application Ser. No. 13/484,584, entitled "Surgical Instrument with Orientation Sensing," filed on even date herewith, now U.S. Pat. No. 9,572,592, issued Feb. 21, 2017, the disclosure of which are incorporated by reference herein. Of course other sources for determining the procedure will be apparent to one of ordinary skill in the art in view of the teachings herein. By way of example only, determining the procedure may comprise utilizing a predetermined modular end effector with a surgical instrument configured for a specific procedure such that the procedure configuration data is communicated to a control module and/or controller, such as control module (12) and/or controller (790), for surgical instrument (700). In addition, or in the alternative, such a procedure determination may be accomplished via a user selection of a procedure configuration data through a user interface, such as that disclosed in U.S. patent application Ser. No. 13/484,584, entitled "Surgical Instrument with Orientation Sensing," filed on even date herewith, now U.S. Pat. No. 9,572,592, issued Feb. 21, 2017,; through a user selection via a generator, such as generator (40); and/or otherwise. The procedure configuration data may comprise a range of forces that correspond to a range of forces that may be applied to blade (730) of instrument (700) during the determined procedure, as will be described in greater detail below. For example, a first range of forces associated with a first procedure may correspond to a thoracic procedure, while a second set of forces associated with a second procedure may correspond to an general surgical procedure. Still other data may be loaded and/or otherwise used from the step (1400) of determining the procedure to be performed as will be apparent to one of ordinary skill in the art in view of the teachings herein. Of course the foregoing is merely optional and may be omitted entirely.

At step (1410), a single activation or power button (708) is initially activated by the user. As noted above, activation button (708) may include a trigger, a capacitive touch sensor, a resistive touch sensor, an electromechanical button, and/or any other activation button (708) as will be apparent to one of ordinary skill in the art in view of the teachings herein. The use of a single activation button (708) may simplify instrument (700) such that a user need not switch between various energy level setting buttons, such as a max or min energy toggle, during use of the instrument (700), though this is merely optional. At step (1420), controller (790) monitors directional force sensor assembly (750). As described herein, controller (790) is operable to determine both the magnitude and direction of force applied to blade (730). At step (1430), controller (790) compares the magnitude of the force from directional force sensor assembly (750) to a predetermined setting or range, such as that loaded during optional step (1400) and/or to a predetermined range accessible by controller (790) (e.g., on a storage device electrically coupled to controller (790)). Such a predetermined range may correspond to an optimal range of forces for the procedure determined during step (1400); to a predetermined range based upon an energy setting applied to transducer (710), such as that determined above at step (1240) of FIG. 21; and/or to any other predetermined range as will be apparent to one of ordinary skill in the art in view of the teachings herein. By way of example only, a merely exemplary range of forces is shown in graphical form in FIG. 24 as band (1550).

Figure 24:
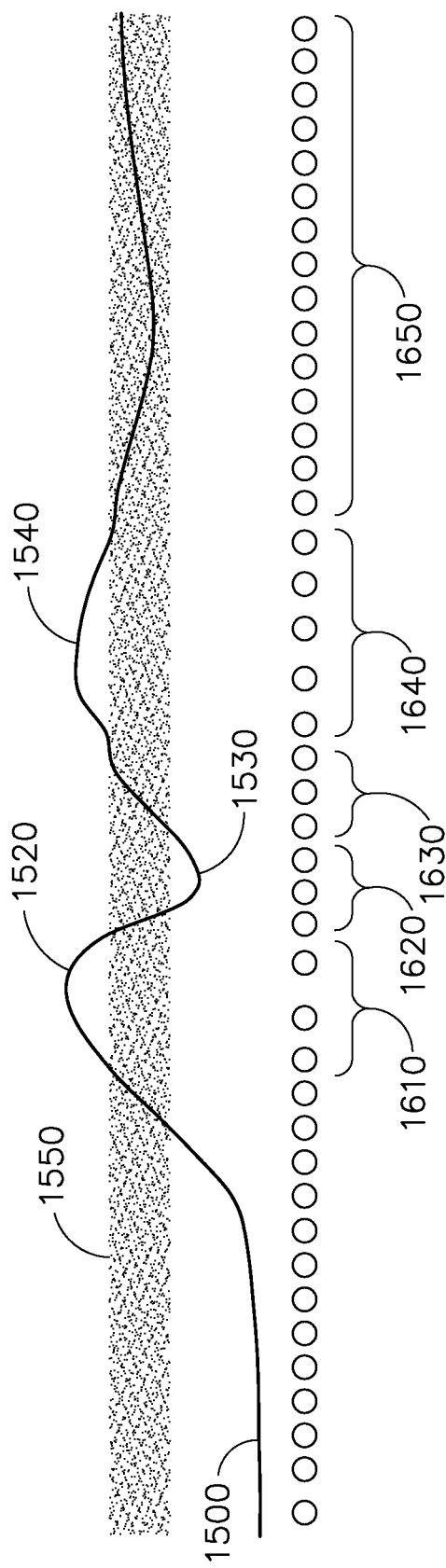
FIG. 24 depicts a graphical view of force on a blade over time relative to an optimal force zone and the corresponding user feedback.

At step (1440), controller (790) determines whether the detected magnitude of force applied to blade (730) is outside of the predetermined range from step (1430). As shown in FIG. 24, line (1500) corresponds to the magnitude of force output from directional force sensor assembly (750). Where line (1500) remains within band (1550), the force applied to blade (730) is within the predetermined range from step (1430). Accordingly, at step (1450) of FIG. 23, a speaker or other audio generating device outputs or maintains a predetermined audio tone. By way of example only, such an audio tone may comprise a periodic clicking or beeping noise, such as that indicated by dots in regions (1630, 1650) of FIG. 24. Of course other indicators may be used as well, such as a visual indicator of dots and/or a line (1500) shown in FIG. 24, a plurality of LEDs, tactile vibrations, and/or any other indicator as will be apparent to one of ordinary skill in the art in view of the teachings herein.

If the controller (790) determines at step (1440) that the detected magnitude of force applied to blade (730) is higher than the maximum of the predetermined range, then the speaker or other audio generating device slows the audio tone at step (1460). As shown in FIG. 24, where line (1500) exceeds band (1550) at regions (1520, 1540), then the force applied to blade (730) is too high relative to the predetermined range from step (1430). The corresponding audio tone of the present example comprises a slowing periodic clicking or beeping noise, such as that indicated by dots in regions (1610, 1640) of FIG. 24. By way of example only, such a slowing down audible signal may produce a sound similar to a chainsaw bogging down. Of course other indicators may be used as well, such as a visual indicator of dots and/or a line (1500) of FIG. 24; a decrease of intensity, blinking, and/or number of illuminated LEDs; a reduced number of tactile vibrations; and/or any other indicator as will be apparent to one of ordinary skill in the art in view of the teachings herein.

If the controller (790) determines at step (1440) that the detected magnitude of force applied to blade (730) is lower than the maximum of the predetermined range, then the speaker or other audio generating device increases the audio tone at step (1470). As shown in FIG. 24, where line (1500) drops below band (1550) at region (1530), then the force applied to blade (730) is too low relative to the predetermined range from step (1430). The corresponding audio tone of the present example comprises a sped-up periodic clicking or beeping noise, such as that indicated by dots in region (1620) of FIG. 24. By way of example only, such a sped-up audible signal may produce a sound similar to a freewheeling and/or other high pitched noise. Of course other indicators may be used as well, such as a visual indicator of dots and/or a line (1500) of FIG. 24; an increase of intensity, blinking, and/or number of illuminated LEDs; an increased number of tactile vibrations; and/or any other indicator as will be apparent to one of ordinary skill in the art in view of the teachings herein.

Once controller (790) determines the force and adjusts and/or maintains the audible signal in accordance with steps (1450, 1460, 1470), controller (790) returns to monitoring the sensors at step (1420). Accordingly, the controller is then operable to adjust the audible signal or other indicator in response to the user's subsequent usage. Thus, the feedback permits a user to adjust the force exerted on blade (730) to operate the instrument (700) within the predetermined range and/or band (1550). A user may adapt to use the instrument (700) more effectively using the feedback of the present description. In addition, in combination with the configuration described in reference to FIG. 21 and/or any other suitable configuration as will be apparent to one of ordinary skill in the art in view of the teachings herein, the feedback from the present configuration of FIG. 23 may be used to assist the user in responding to changes in the tissue (e.g., different densities, thicknesses, compositions, etc.). Of course still other configurations will be apparent to one of ordinary skill in the art in view of the teachings herein.

VII. Miscellaneous

As noted above, a storage device may be used to store operating parameters, other data, and/or control algorithms, etc. associated with the various kinds of surgical instruments referred to herein. Such information may be preloaded and/or later updated; and may dictate performance characteristics of the surgical instrument. For instance, software/firmware/information on the storage device may influence power delivery from a generator or other power source, which may in turn affect the performance of the end effector as driven by the power source. In some systems, a generator, power source, control module, and/or other component provides a baseline functionality for the surgical instrument; while software/firmware/information on the storage device provides enhanced functionality (e.g., active dampening, surgeon gesture recognition, enhanced user feedback, etc.). It should be understood that a storage device may take any suitable form, including but not limited to a chip, card, or other type of storage medium as will be apparent to those of ordinary skill in the art in view of the teachings herein. It should also be understood that the storage device may be located in any suitable location within the system. By way of example only, the storage device may be located in a removable cartridge, such as the various removable cartridges described in U.S. patent application Ser. No. 13/426,760, entitled "Method and Apparatus for Programming Modular Surgical Instrument," filed Mar. 22, 2012, now U.S. Pat. No. 9,364,249, issued Jun. 14, 2016, the disclosure of which is incorporated by reference herein, the disclosure of which is incorporated by reference herein. As another merely illustrative example, the storage device may be embodied in an online remote server that is in communication with the surgical instrument and/or generator, etc., such as in the system described in U.S. patent application Ser. No. 13/426,792, entitled "Surgical Instrument Usage Data Management," filed Mar. 22, 2012, published as U.S. Pub. No. 2013/0253480 on Sep. 26, 2013, the disclosure of which is incorporated by reference herein, the disclosure of which is incorporated by reference herein. As yet another merely illustrative example, the storage device may be included as either an integral component or a removable component of the end effector, shaft, handpiece, cable, and/or other part of the surgical instrument. Various other suitable locations for a storage device will be apparent to those of ordinary skill in the art in view of the teachings herein. It should also be understood that the storage device may store surgeon usage data, patient data, and/or other kinds of data as described herein, such that the storage device may receive additional data during use of the surgical instrument.

In some versions, a manufacturer or seller of a surgical instrument provides the surgical instrument as a single use instrument, with the appropriate software/firmware/information preloaded on the storage device for the single use. In some such versions, the software/firmware/information is inaccessible or inoperable after the surgical instrument is used for a predetermined number of uses. For instance, if the instrument is designed for a specified number of uses, the software/firmware/information may be at least partially deleted or disabled at some point after the predefined design life is exceeded. In the case where either the manufacturer or another party chooses to reprocess/resterilize the device beyond the predefined design life, the reprocessed/resterilized surgical instrument may still be at least partially operable, but with reduced functionality. For instance, a surgeon may still be able to suitably use the reprocessed/resterilized surgical instrument, but the instrument may lack enhanced functionality (e.g., active dampening, surgeon gesture recognition, enhanced user feedback, etc.) that was otherwise originally provided through the software/firmware/information stored in the storage device. In some versions, the storage device allows the manufacturer or seller to segment the performance of the instrument according to the functional needs of the customer. If the customer only needs limited functionality to perform specific surgeries such cholecystectomy, then the storage device will be loaded with the appropriate software/firmware/information. If the customer needs enhanced performance for difficult surgeries or to expand the potential operating performance of the device if the surgery is more difficult than anticipated, then the storage device may be loaded accordingly. In either case, some versions may permit a manufacturer or seller to adjust the functionality of the surgical instrument to meet the needs of the customer with the customer defined functionality from software/firmware/information on the storage device; and to meet a different set of customer defined needs without the enhanced functionality.

Finally, it should be understood that software/firmware/information in a storage device as described herein need not necessarily be influenced by any kind of sensors in the surgical instrument. For instance, the surgical instrument may simply lack sensors altogether; or the storage device may not be in communication with sensors.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
   (a) a body assembly comprising an energy component, wherein the energy component is operable at a plurality of energy settings;
   (b) a control module;
   (c) a directional force sensor assembly, wherein the directional force sensor assembly is associated with the energy component, wherein the directional force sensor assembly is communicatively coupled to the control module; and
   (d) an end effector, wherein the end effector is coupled to the energy component, wherein the directional force sensor assembly encompasses a cross-sectional perimeter of a longitudinal portion of the end effector;
   wherein the directional force sensor assembly is operable to detect a magnitude and a direction of a force applied to the end effector relative to the body assembly, wherein the control module is configured to operate the energy component at a first energy setting in response to the output of the directional force sensor assembly detecting a first magnitude and a first direction of a first force.

2. The apparatus of claim 1 wherein the first energy setting is an unpowered state.

3. The apparatus of claim 1 wherein the directional force sensor assembly comprises a piezoelectric disc.

4. The apparatus of claim 3 wherein the piezoelectric disc is coupled to the energy component.

5. The apparatus of claim 3 wherein the piezoelectric disc is coupled to the end effector.

6. The apparatus of claim 1 wherein the directional force sensor assembly comprises at least one accelerometer.

7. The apparatus of claim 1 wherein the directional force sensor assembly comprises a piezoresistive element, wherein the body assembly comprises a casing, wherein the piezoresistive element is associated with the casing.

8. The apparatus of claim 7 wherein the end effector is coupleable to the casing, wherein the end effector comprises a finger operable to compress the piezoresistive element in response to a force applied to the end effector.

9. The apparatus of claim 1 wherein the directional force sensor assembly comprises a piezoresistive element, wherein the energy component comprises a waveguide, wherein the piezoresistive element comprises a piezoresistive strip coupled to the waveguide.

10. The apparatus of claim 1 wherein the directional force sensor assembly comprises a Hall Effect sensor.

11. The apparatus of claim 1 wherein the energy component comprises an ultrasonic transducer.

12. The apparatus of claim 1 wherein the end effector comprises an RF electrode.

13. The apparatus of claim 1 wherein the end effector comprises a staple driving assembly.

14. The apparatus of claim 1 wherein the control module is configured to operate the energy component at a second energy setting in response to the output of the directional force sensor assembly detecting a second force.

15. The apparatus of claim 1 further comprises an activation feature operable by a user, wherein the control module is operable to operate the energy component at a first energy setting in response to both the output of the directional force sensor assembly detecting a first force and a user operating the activation feature.

16. An apparatus comprising:
   (a) a body assembly comprising an energy component, wherein the energy component is operable at a plurality of energy settings;
   (b) a control module;
   (c) an end effector, wherein the end effector is coupled to the energy component; and
   (d) a directional force sensor assembly associated with the energy component, wherein the direction force sensor assembly is communicatively coupled to the control module, wherein the directional force sensor assembly comprises:
      i. an annular array of force sensing elements fixed to the body assembly, and
      ii. a finger associated with the end effector, wherein the finger is configured to deflect toward a portion of the annular array of force sensing elements in response to a force applied to the end effector,
   wherein the directional force sensor assembly is operable to detect a magnitude and a direction of a force applied to the end effector relative to the body assembly, wherein the control module is configured to operate the energy component at a first energy setting in response to the output of the directional force sensor assembly detecting a magnitude and a direction of a first force.

17. The apparatus of claim 16, wherein the finger is attached to a sheath surrounding the end effector.

18. An apparatus comprising:
   (a) a body assembly comprising an energy component, wherein the energy component is operable at a plurality of energy settings;
   (b) a control module;
   (c) an end effector, wherein the end effector is coupled to the energy component; and
   (d) a directional force sensor assembly comprising a plurality of force sensing elements, wherein the plurality of force sensing elements encompass the end effector, wherein the directional force sensor assembly is associated with the energy component, wherein the directional force sensor assembly is communicatively coupled to the control module;
   wherein the directional force sensor assembly is operable to detect a magnitude and a direction of a force applied to the end effector relative to the body assembly, wherein the control module is configured to operate the energy component at a first energy setting in response to the output of the directional force sensor assembly detecting a first magnitude and a first direction of a first force.

19. An apparatus comprising:
   (a) a body assembly comprising an energy component, wherein the energy component is operable at a plurality of energy settings;
   (b) a control module;
   (c) an end effector, wherein the end effector is coupled to the energy component; and
   (d) a directional force sensor assembly, wherein the directional force sensor assembly is associated with the energy component, wherein the directional force sensor assembly is communicatively coupled to the control module,
   wherein the directional force sensor assembly comprises:

i. an annular array of hall effect sensors surrounding a portion of the end effector, wherein the annular array of hall effect sensors extend toward the body assembly, and ii. a magnet disposed within the end effector;

wherein the directional force sensor assembly is operable to detect a magnitude and a direction of a force applied to the end effector relative to the body assembly, wherein the control module is configured to operate the energy component at a first energy setting in response to the output of the directional force sensor assembly detecting a first magnitude and a first direction of a first force.

20. The apparatus of claim 19, wherein the end effector includes a transverse hole, wherein the magnet is disposed within the transverse hole.

21. The apparatus of claim 20, wherein the magnet is surrounded by a layer of silicone.

\* \* \* \* \*